United States Patent
Powell et al.

(10) Patent No.: US 9,376,355 B2
(45) Date of Patent: Jun. 28, 2016

(54) METHOD AND SYSTEMS FOR PROCESSING LIGNIN DURING HYDROTHERMAL DIGESTION OF CELLULOSIC BIOMASS SOLIDS WHILE PRODUCING A MONOHYDRIC ALCOHOL FEED

(71) Applicant: SHELL OIL COMPANY, Houston, TX (US)

(72) Inventors: Joseph Broun Powell, Houston, TX (US); Kimberly Ann Johnson, Richmond, TX (US)

(73) Assignee: Shell Oil Company, Houston, TX (US)

( * ) Notice: Subject to any disclaimer, the term of this patent is extended or adjusted under 35 U.S.C. 154(b) by 157 days.

(21) Appl. No.: 14/067,282

(22) Filed: Oct. 30, 2013

(65) Prior Publication Data
US 2014/0121418 A1    May 1, 2014

Related U.S. Application Data

(60) Provisional application No. 61/720,774, filed on Oct. 31, 2012.

(51) Int. Cl.
| | | |
|---|---|---|
| C07C 27/04 | (2006.01) | |
| C10G 1/00 | (2006.01) | |
| C10G 1/06 | (2006.01) | |
| C10G 3/00 | (2006.01) | |
| D21C 3/20 | (2006.01) | |
| C07C 29/132 | (2006.01) | |
| C07C 29/60 | (2006.01) | |
| C07C 41/18 | (2006.01) | |

(52) U.S. Cl.
CPC .............. C07C 27/04 (2013.01); C07C 29/132 (2013.01); C07C 29/60 (2013.01); C07C 41/18 (2013.01); C10G 1/002 (2013.01); C10G 1/065 (2013.01); C10G 3/50 (2013.01); D21C 3/20 (2013.01); C10G 2300/1014 (2013.01); C10G 2300/302 (2013.01); Y02P 30/20 (2015.11)

(58) Field of Classification Search
CPC ...... C07C 27/04; C07C 29/132; C07C 29/60; C07C 41/18; C10G 1/002; C10G 1/065; C10G 3/50; C10G 2300/1014; C10G 2300/302; D21C 3/20
See application file for complete search history.

(56) References Cited

U.S. PATENT DOCUMENTS

| | | |
|---|---|---|
| 6,030,915 A | 2/2000 | de Boer |
| 6,127,229 A | 10/2000 | Chu et al. |
| 8,262,905 B2 | 9/2012 | Gabrielov |
| 2008/0216391 A1 | 9/2008 | Cortright et al. |
| 2010/0236988 A1 | 9/2010 | Gabrielov et al. |
| 2011/0312050 A1 | 12/2011 | Zhang et al. |
| 2012/0151827 A1 | 6/2012 | Powell et al. |
| 2012/0152836 A1 | 6/2012 | Powell et al. |
| 2012/0156742 A1 | 6/2012 | Powell et al. |
| 2012/0167876 A1 | 7/2012 | Qiao et al. |
| 2012/0317872 A1 | 12/2012 | Powell et al. |
| 2013/0109896 A1 | 5/2013 | Powell et al. |
| 2013/0152457 A1 | 6/2013 | Powell et al. |
| 2013/0152458 A1 | 6/2013 | Powell et al. |
| 2014/0117275 A1 | 5/2014 | Powell et al. |
| 2014/0117276 A1 | 5/2014 | Powell et al. |
| 2014/0117277 A1 | 5/2014 | Powell et al. |
| 2014/0121420 A1 | 5/2014 | Powell et al. |
| 2014/0121423 A1 | 5/2014 | Powell et al. |

FOREIGN PATENT DOCUMENTS

| | | | |
|---|---|---|---|
| EP | 2182047 | 5/2010 | |
| FR | 2955118 | 7/2011 | |
| FR | 2974109 | * 10/2012 | ........... B01J 27/0515 |
| WO | 2012060961 | 5/2012 | |
| WO | WO2012174103 | 12/2012 | |
| WO | WO2013089798 | 6/2013 | |
| WO | WO2013089799 | 6/2013 | |
| WO | 2014004844 | 1/2014 | |
| WO | 2014004859 | 1/2014 | |
| WO | 2014004867 | 1/2014 | |
| WO | WO2014004842 | 1/2014 | |
| WO | WO2014004848 | 1/2014 | |
| WO | WO2014004859 | 1/2014 | |
| WO | WO2014004867 | 1/2014 | |

OTHER PUBLICATIONS

English translation of FR2974109, pp. 1-19.*
Luo, Chen et al., Luo, Chen et al., Cellulose Conversion into Polyols Catalyzed by Reversibly Formed Acids.
ISR—PCT/US2013/066660, International Search Report dated Mar. 10, 2014.
ISR—PCT/US2013/066666, International Search Report dated Feb. 14, 2014.
ISR—PCT/US2013/066631, International Search Report dated Feb. 21, 2014.
ISR—PCT/US2013/066623, International Search Report dated Feb. 12, 2014.

(Continued)

Primary Examiner — Paul A Zucker
Assistant Examiner — Mark Luderer

(57) ABSTRACT

Digestion of cellulosic biomass solids may be complicated by release of lignin therefrom. Methods for digesting cellulosic biomass solids may comprise: providing cellulosic biomass solids in the presence of a digestion solvent, molecular hydrogen, and a slurry catalyst capable of activating molecular hydrogen; at least partially converting the cellulosic biomass solids into a phenolics liquid phase comprising lignin, an aqueous phase comprising a glycol derived from the cellulosic biomass solids, and an optional light organics phase; wherein at least a portion of the slurry catalyst accumulates in the phenolics liquid phase as it forms; combining the glycol with the phenolics liquid phase, thereby forming a combined phase; and heating the combined phase in the presence of molecular hydrogen; wherein heating the combined phase reduces the viscosity of the phenolics liquid phase and transforms at least a portion of the glycol into a monohydric alcohol.

38 Claims, 1 Drawing Sheet

(56) References Cited

OTHER PUBLICATIONS

ISR—PCT/US2013/066653, International Search Report dated Mar. 10, 2014.
ISR—PCT/US2013/066625, International Search Report dated Mar. 10, 2014.
ISR—PCT/US2013/066638, International Search Report dated Dec. 13, 2013.
ISR—PCT/US2013/066642, International Search Report dated Dec. 12, 2013.

* cited by examiner

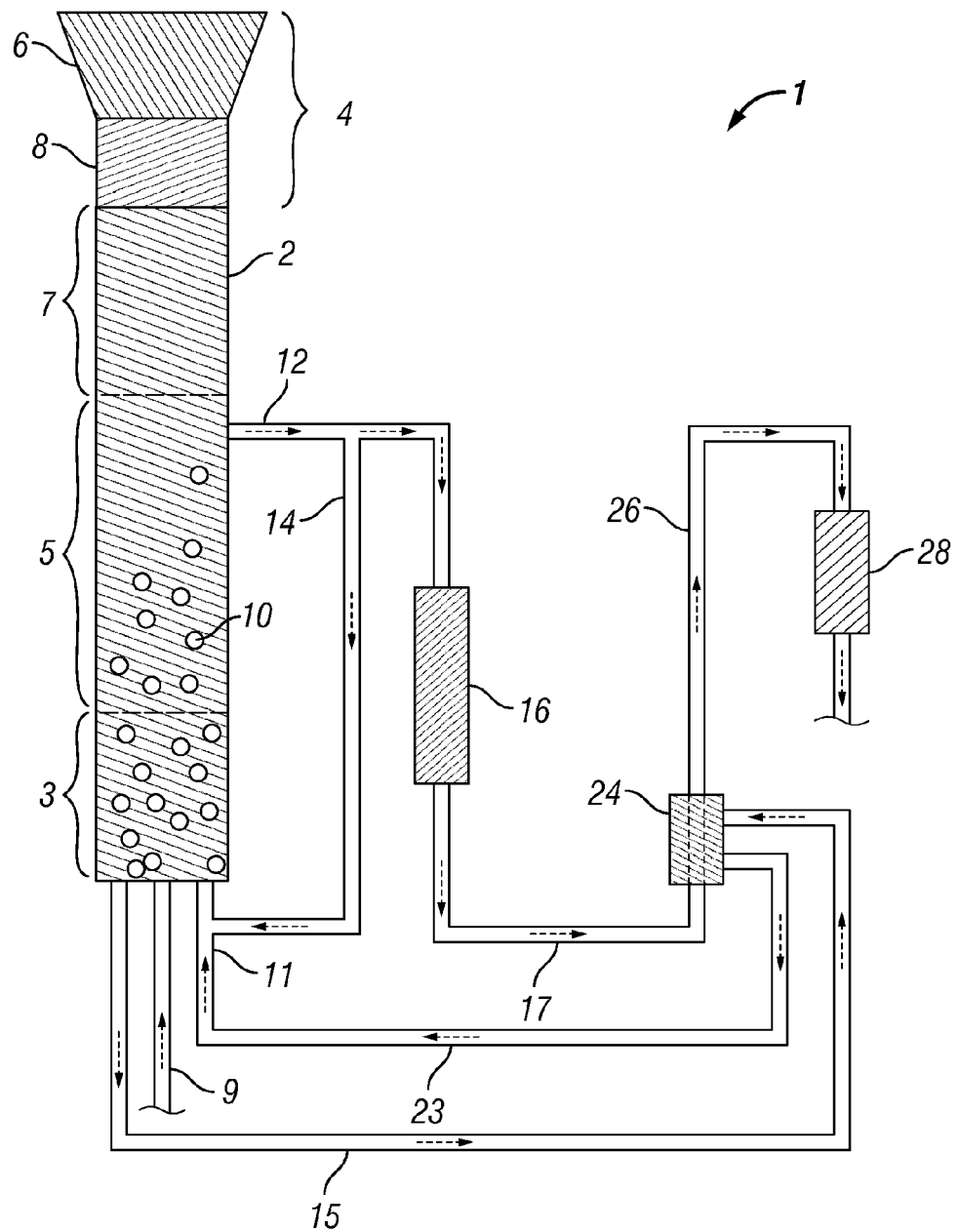

METHOD AND SYSTEMS FOR PROCESSING LIGNIN DURING HYDROTHERMAL DIGESTION OF CELLULOSIC BIOMASS SOLIDS WHILE PRODUCING A MONOHYDRIC ALCOHOL FEED

The present application claims the benefit of pending U.S. Provisional Patent Application Ser. No. 61/720,774, filed Oct. 31, 2012 the entire disclosure of which is hereby incorporated by reference.

FIELD OF THE INVENTION

The present disclosure generally relates to digestion of cellulosic biomass solids, and, more specifically, to methods for processing a phenolics liquid phase comprising lignin that may be obtained in conjunction with hydrothermal digestion of cellulosic biomass solids, while producing a monohydric alcohol.

BACKGROUND OF THE INVENTION

A number of substances of commercial significance may be produced from natural sources, including biomass. Cellulosic biomass may be particularly advantageous in this regard due to the versatility of the abundant carbohydrates found therein in various forms. As used herein, the term "cellulosic biomass" refers to a living or recently living biological material that contains cellulose. The lignocellulosic material found in the cell walls of higher plants is the world's largest source of carbohydrates. Materials commonly produced from cellulosic biomass may include, for example, paper and pulpwood via partial digestion, and bioethanol by fermentation.

Plant cell walls are divided into two sections: primary cell walls and secondary cell walls. The primary cell wall provides structural support for expanding cells and contains three major polysaccharides (cellulose, pectin, and hemicellulose) and one group of glycoproteins. The secondary cell wall, which is produced after the cell has finished growing, also contains polysaccharides and is strengthened through polymeric lignin that is covalently crosslinked to hemicellulose. Hemicellulose and pectin are typically found in abundance, but cellulose is the predominant polysaccharide and the most abundant source of carbohydrates. The complex mixture of constituents that is co-present with the cellulose can make its processing difficult, as discussed hereinafter. Lignin, in particular, may be an especially difficult constituent to deal with.

Significant attention has been placed on developing fossil fuel alternatives derived from renewable resources. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane).

Moreover, conventional bio-based processes have produced intermediates in dilute aqueous solutions (>50% water by weight) that are difficult to further process. Energy- and cost-efficient processes for processing cellulosic biomass into fuel blends having similar compositions to fossil fuels would be highly desirable to address the foregoing issues and others.

When converting cellulosic biomass into fuel blends and other materials, cellulose and other complex carbohydrates therein can be extracted and transformed into simpler organic molecules, which can be further reformed thereafter. Fermentation is one process whereby complex carbohydrates from cellulosic biomass may be converted into a more usable form. However, fermentation processes are typically slow, require large volume reactors and high dilution conditions, and produce an initial reaction product having a low energy density (ethanol). Digestion is another way in which cellulose and other complex carbohydrates may be converted into a more usable form. Digestion processes can break down cellulose and other complex carbohydrates within cellulosic biomass into simpler, soluble carbohydrates that are suitable for further transformation through downstream reforming reactions. As used herein, the term "soluble carbohydrates" refers to monosaccharides or polysaccharides that become solubilized in a digestion process. Although the underlying chemistry is understood behind digesting cellulose and other complex carbohydrates and further transforming simple carbohydrates into organic compounds reminiscent of those present in fossil fuels, high-yield and energy-efficient digestion processes suitable for converting cellulosic biomass into fuel blends have yet to be developed. In this regard, the most basic requirement associated with converting cellulosic biomass into fuel blends using digestion and other processes is that the energy input needed to bring about the conversion should not be greater than the available energy output of the product fuel blends. This basic requirement leads to a number of secondary issues that collectively present an immense engineering challenge that has not been solved heretofore.

The issues associated with converting cellulosic biomass into fuel blends in an energy- and cost-efficient manner using digestion are not only complex, but they are entirely different than those that are encountered in the digestion processes commonly used in the paper and pulpwood industry. Since the intent of cellulosic biomass digestion in the paper and pulpwood industry is to retain a solid material (e.g., wood pulp), incomplete digestion is usually performed at low temperatures (e.g., less than about 100° C.) for a fairly short period of time. In contrast, digestion processes suitable for converting cellulosic biomass into fuel blends and other materials are ideally configured to maximize yields by solubilizing as much of the original cellulosic biomass charge as possible in a high-throughput manner. Paper and pulpwood digestion processes also typically remove lignin from the raw cellulosic biomass prior to pulp formation. Although digestion processes used in connection with forming fuel blends and other materials may likewise remove lignin prior to digestion, these extra process steps may impact the energy efficiency and cost of the biomass conversion process. The presence of lignin during high-conversion cellulosic biomass digestion may be particularly problematic.

Production of soluble carbohydrates for use in fuel blends and other materials via routine modification of paper and pulpwood digestion processes is not believed to be economically feasible for a number of reasons. Simply running the digestion processes of the paper and pulpwood industry for a longer period of time to produce more soluble carbohydrates is undesirable from a throughput standpoint. Use of digestion promoters such as strong alkalis, strong acids, or sulfites to accelerate the digestion rate can increase process costs and complexity due to post-processing separation steps and the possible need to protect downstream components from these agents. Accelerating the digestion rate by increasing the digestion temperature can actually reduce yields due to thermal degradation of soluble carbohydrates that can occur at elevated digestion temperatures, particularly over extended periods of time. Once produced by digestion, soluble carbohydrates are very reactive and can rapidly degrade to produce caramelans and other heavy ends degradation products, especially under higher temperature conditions, such as above about 150° C. Use of higher digestion temperatures can also be undesirable from an energy efficiency standpoint. Any of these difficulties can defeat the economic viability of fuel blends derived from cellulosic biomass.

One way in which soluble carbohydrates can be protected from thermal degradation is through subjecting them to one or more catalytic reduction reactions, which may include hydrogenation and/or hydrogenolysis reactions. Stabilizing soluble carbohydrates through conducting one or more catalytic reduction reactions may allow digestion of cellulosic biomass to take place at higher temperatures than would otherwise be possible without unduly sacrificing yields. Depending on the reaction conditions and catalyst used, reaction products formed as a result of conducting one or more catalytic reduction reactions on soluble carbohydrates may comprise one or more alcohol functional groups, particularly including triols, diols, monohydric alcohols, and any combination thereof, some of which may also include a residual carbonyl functionality (e.g., an aldehyde or a ketone). Such reaction products are more thermally stable than soluble carbohydrates and may be readily transformable into fuel blends and other materials through conducting one or more downstream reforming reactions. In addition, the foregoing types of reaction products are good solvents in which a hydrothermal digestion may be performed, thereby promoting solubilization of soluble carbohydrates as their reaction products. Although a digestion solvent may also promote solubilization of lignin, this material may still be difficult to effectively process due to its poor solubility and precipitation propensity.

A particularly effective manner in which soluble carbohydrates may be formed and converted into more stable compounds is through conducting the hydrothermal digestion of cellulosic biomass in the presence of molecular hydrogen and a slurry catalyst capable of activating the molecular hydrogen (also referred to herein as a "hydrogen-activating catalyst"). That is, in such approaches (termed "in situ catalytic reduction reaction processes" herein), the hydrothermal digestion of cellulosic biomass and the catalytic reduction of soluble carbohydrates produced therefrom may take place in the same vessel. As used herein, the term "slurry catalyst" will refer to a catalyst comprising fluidly mobile catalyst particles that can be at least partially suspended in a fluid phase via gas flow, liquid flow, mechanical agitation, or any combination thereof. If the slurry catalyst is sufficiently well distributed in the cellulosic biomass, soluble carbohydrates formed during hydrothermal digestion may be intercepted and converted into more stable compounds before they have had an opportunity to significantly degrade, even under thermal conditions that otherwise promote their degradation. Without adequate catalyst distribution being realized, soluble carbohydrates produced by in situ catalytic reduction reaction processes may still degrade before they have had an opportunity to encounter a catalytic site and undergo a stabilizing reaction. In situ catalytic reduction reaction processes may also be particularly advantageous from an energy efficiency standpoint, since hydrothermal digestion of cellulosic biomass is an endothermic process, whereas catalytic reduction reactions are exothermic. Thus, the excess heat generated by the in situ catalytic reduction reaction(s) may be utilized to drive the hydrothermal digestion with little opportunity for heat transfer loss to occur, thereby lowering the amount of additional heat energy input needed to conduct the digestion.

Another issue associated with the processing of cellulosic biomass into fuel blends and other materials is created by the need for high conversion percentages of a cellulosic biomass charge into soluble carbohydrates. Specifically, as cellulosic biomass solids are digested, their size gradually decreases to the point that they can become fluidly mobile. As used herein, cellulosic biomass solids that are fluidly mobile, particularly cellulosic biomass solids that are about 3 mm in size or less, will be referred to as "cellulosic biomass fines." Cellulosic biomass fines can be transported out of a digestion zone of a system for converting cellulosic biomass and into one or more zones where solids are unwanted and can be detrimental. For example, cellulosic biomass fines have the potential to plug catalyst beds, transfer lines, valving, and the like. Furthermore, although small in size, cellulosic biomass fines may represent a non-trivial fraction of the cellulosic biomass charge, and if they are not further converted into soluble carbohydrates, the ability to attain a satisfactory conversion percentage may be impacted. Since the digestion processes of the paper and pulpwood industry are run at relatively low cellulosic biomass conversion percentages, smaller amounts of cellulosic biomass fines are believed to be generated and have a lesser impact on those digestion processes.

In addition to the desired carbohydrates, other substances may be present within cellulosic biomass that can be especially problematic to deal with in an energy- and cost-efficient manner. Sulfur- and/or nitrogen-containing amino acids or other catalyst poisons may be present in cellulosic biomass. If not removed, these catalyst poisons can impact the catalytic reduction reaction(s) used to stabilize soluble carbohydrates, thereby resulting in process downtime for catalyst regeneration and/or replacement and reducing the overall energy efficiency when restarting the process. This issue is particularly significant for in situ catalytic reduction reaction processes, where there is minimal opportunity to address the presence of catalyst poisons, at least without significantly increasing process complexity and cost. As mentioned above, lignin can also be particularly problematic to deal with if it is not removed prior to beginning digestion. During cellulosic biomass processing, the significant quantities of lignin present in cellulosic biomass may lead to fouling of processing equipment, potentially leading to costly system down time. The significant lignin quantities can also lead to realization of a relatively low conversion of the cellulosic biomass into useable substances per unit weight of feedstock.

As evidenced by the foregoing, the efficient conversion of cellulosic biomass into fuel blends and other materials is a complex problem that presents immense engineering challenges. The present disclosure addresses these challenges and provides related advantages as well.

SUMMARY OF THE INVENTION

The present disclosure generally relates to digestion of cellulosic biomass solids, and, more specifically, to methods for processing a phenolics liquid phase comprising lignin that may be obtained in conjunction with hydrothermal digestion of cellulosic biomass solids, while producing a monohydric alcohol.

In some embodiments, the present disclosure provides methods comprising: providing cellulosic biomass solids in the presence of a digestion solvent, molecular hydrogen, and a slurry catalyst capable of activating molecular hydrogen; at least partially converting the cellulosic biomass solids into a phenolics liquid phase comprising lignin, an aqueous phase comprising a glycol derived from the cellulosic biomass solids, and an optional light organics phase; wherein at least a portion of the slurry catalyst accumulates in the phenolics liquid phase as it forms; combining the glycol with the phenolics liquid phase, thereby forming a combined phase; and heating the combined phase in the presence of molecular hydrogen; wherein heating the combined phase reduces the viscosity of the phenolics liquid phase and transforms at least a portion of the glycol into a monohydric alcohol.

In some embodiments, the present disclosure provides methods comprising: providing cellulosic biomass solids in the presence of a digestion solvent, molecular hydrogen, and a slurry catalyst capable of activating molecular hydrogen; heating the cellulosic biomass solids to a first temperature and forming a phenolics liquid phase comprising lignin, an aqueous phase comprising a glycol derived from the cellulosic biomass solids, and an optional light organics phase; wherein at least a portion of the slurry catalyst accumulates in the phenolics liquid phase as it forms; separating the phenolics liquid phase from the aqueous phase and the cellulosic biomass solids; removing at least a portion of the water from the aqueous phase, thereby producing a dried glycol; combining the dried glycol with the phenolics liquid phase, thereby forming a combined phase; and heating the combined phase to a second temperature in the presence of molecular hydrogen, the second temperature being sufficient to reduce the viscosity of the phenolics liquid phase and transform at least a portion of the dried glycol into a monohydric alcohol; wherein the first temperature is lower than the second temperature.

The features and advantages of the present disclosure will be readily apparent to one having ordinary skill in the art upon a reading of the description of the embodiments that follows.

BRIEF DESCRIPTION OF THE DRAWING

The following FIGURE is included to illustrate certain aspects of the present disclosure, and should not be viewed as an exclusive embodiment. The subject matter disclosed is capable of considerable modifications, alterations, combinations, and equivalents in form and function, as will occur to one having ordinary skill in the art and the benefit of this disclosure.

FIG. 1 shows a schematic of an illustrative biomass conversion system in which a phenolics liquid phase may form and be further processed.

DETAILED DESCRIPTION

The present disclosure generally relates to digestion of cellulosic biomass solids, and, more specifically, to methods for processing a phenolics liquid phase comprising lignin that may be obtained in conjunction with hydrothermal digestion of cellulosic biomass solids, while producing a monohydric alcohol.

In the embodiments described herein, the digestion rate of cellulosic biomass solids may be accelerated in the presence of a digestion solvent. In some instances, the digestion solvent may be maintained at elevated pressures that keep the digestion solvent in a liquid state when raised above its normal boiling point. Although the more rapid digestion rate of cellulosic biomass solids under elevated temperature and pressure conditions may be desirable from a throughput standpoint, soluble carbohydrates may be susceptible to degradation at elevated temperatures, as discussed above. As further discussed above, one approach for addressing the degradation of soluble carbohydrates during hydrothermal digestion is to conduct an in situ catalytic reduction reaction process so as to convert the soluble carbohydrates into more stable compounds as soon as possible after their formation.

Although digesting cellulosic biomass solids by an in situ catalytic reduction reaction process may be particularly advantageous for at least the reasons noted above, successfully executing such a coupled approach may be problematic in other aspects. One significant issue that may be encountered is that of adequate catalyst distribution within the digesting cellulosic biomass solids, since insufficient catalyst distribution can result in poor stabilization of soluble carbohydrates. Although a catalyst might be pre-mixed or co-blended with cellulosic biomass solids and then subjected to an in situ catalytic reduction reaction process, these solutions may still produce inadequate catalyst distribution and present significant engineering challenges that markedly increase process complexity and operational costs. In contrast, the present inventors discovered a relatively simple and low cost engineering solution whereby a slurry catalyst may be effectively distributed within cellulosic biomass solids using fluid flow to convey the slurry catalyst particulates into the interstitial spaces within a charge of cellulosic biomass solids. Although the slurry catalyst may be conveyed into the cellulosic biomass solids using fluid flow from any direction, the present inventors consider it most effective to have at least a portion of the slurry catalyst be conveyed by upwardly directed fluid flow, or at least that upwardly directed fluid flow be present, since such fluid flow may promote expansion of the cellulosic biomass solids and disfavor gravity-induced compaction that occurs during their addition and digestion. In addition, when upwardly directed fluid flow is present, there may be a reduced need to utilize mechanical stirring or like mechanical agitation techniques that might otherwise be needed to obtain an adequate catalyst distribution.

Suitable techniques for using fluid flow to distribute a slurry catalyst within cellulosic biomass solids are described in commonly owned U.S. Patent Application 61/665,727 and 61/665,627, each filed on Jun. 28, 2012 (PCT/US2013/048239 and PCT/US2013/048248) and incorporated herein by reference in its entirety. As described therein, cellulosic biomass solids may have at least some innate propensity for retaining a slurry catalyst being conveyed by fluid flow, and at least a portion of the cellulosic biomass solids may be sized to better promote such retention. In addition, using fluid flow, particularly upwardly directed fluid flow, to force a slurry catalyst to actively circulate through a charge of digesting cellulosic biomass solids may ensure adequate slurry catalyst distribution as well as advantageously reduce thermal gradients that may occur during hydrothermal digestion. As a further advantage, active circulation of the slurry catalyst may address the problem created by the production of cellulosic biomass fines, since they may be co-circulated with the slurry catalyst for continued digestion to take place.

As alluded to above, lignin can be an especially problematic component of cellulosic biomass solids, whose presence during hydrothermal digestion may need to be addressed in some manner, particularly as the lignin content builds. Lignin buildup may be especially problematic in continuously operating processes in which cellulosic biomass solids are supplied and digested on an ongoing basis. During hydrothermal digestion, lignin may either remain undissolved or precipitate from the digestion solvent, either case presenting opportunities for surface fouling. In further regard to the lignin disposition, the present inventors expected that lignin freed from cellulosic biomass solids would reside predominantly in the same location as an alcoholic component being produced by catalytic reduction of soluble carbohydrates. That is, the inventors expected that the lignin and the alcoholic component would be located in the same phase of the digestion medium before the lignin eventually precipitated.

Surprisingly, while digesting cellulosic biomass solids by an in situ catalytic reduction reaction process in the presence of a slurry catalyst, where the cellulosic biomass solids were supplied on an ongoing basis, the present inventors discovered that the lignin predominantly separated as a phenolics liquid phase that was neither fully dissolved nor fully precipitated, but instead formed as a discrete liquid phase that was highly viscous and hydrophobic. In many cases, the phenolics liquid phase was below an aqueous phase containing an alcoholic component derived from the cellulosic biomass solids. Depending on the ratio of water and organic solvent in the digestion solvent, rates of fluid flow, catalyst identity, reaction times and temperatures, and the like, a light organics phase was also sometimes observed, typically above the aqueous phase, where the components of the light organics phase were also derived, at least in part, from the cellulosic materials in the biomass. Components present in the light organics phase included, for example, the desired alcoholic component, including $C_4$ or greater alcohols, and self-condensation products, such as those obtained by the acid-catalyzed Aldol reaction. Formation of the phenolics liquid phase was particularly surprising, since batch processing using only a single addition of cellulosic biomass solids routinely produced only a two-phase mixture of light organics and an aqueous phase containing an alcoholic component. Similar results were obtained using isolated carbohydrates or cellulose under test reaction conditions. Thus, in the presence of excessive lignin quantities or components derived therefrom, at least a portion of the desired alcoholic component derived from the cellulosic biomass solids could either be located in the middle aqueous phase of a three-phase mixture or in the upper phase of a two-phase mixture. This phase behavior alone represented a significant engineering challenge, since a system for further reforming the alcoholic component in the aqueous phase would need to be configured to withdraw the correct phase depending on the particular conditions present during hydrothermal digestion. Ultimately, it was found that the aqueous phase could be separated from the phenolics liquid phase and processed separately, or the two phases could be combined together for processing to further reform the alcoholic component present therein. Moreover, processing of the aqueous phase may take place while simultaneously processing the light organics phase, or the light organics phase may be processed separately. As discussed hereinafter, further processing of the phenolics liquid phase may also be advantageous and contribute to the success of the biomass conversion process. Further, the processing of the phenolics liquid phase can be tied, at least in part, to the processing of the alcoholic component to realize particular process advantages.

The present inventors found that formation of the phenolics liquid phase significantly impacted the ability to successfully conduct an in situ catalytic reduction reaction process, since the phenolics liquid phase increased the difficulty of distributing the slurry catalyst in the cellulosic biomass solids. Specifically, the inventors discovered that the slurry catalyst is readily wetted by the phenolics liquid phase and accumulates therein over time, thereby making the catalyst less available for distribution within the cellulosic biomass solids. Moreover, once the slurry catalyst has been wetted and accumulates in the phenolics liquid phase, the high density and viscosity of this phase may make it difficult to liberate the slurry catalyst therefrom and redistribute it in the cellulosic biomass solids using fluid flow. If enough slurry catalyst becomes unavailable for ready distribution in the cellulosic biomass solids, poor stabilization of soluble carbohydrates as an alcoholic component may occur.

Even more significantly, the inventors found that contact of the phenolics liquid phase with the slurry catalyst was exceedingly detrimental for catalyst life. Without being bound by any theory or mechanism, it is believed that the highly viscous phenolics liquid phase may coat the slurry catalyst and plug pore space therein, thereby blocking at least a portion of the catalytic sites on the slurry catalyst. Furthermore, the inventors found that the high viscosity of the phenolics liquid phase made it difficult to separate the slurry catalyst from this phase. Thus, developing an effective way of removing the slurry catalyst from the phenolics liquid phase, returning the slurry catalyst to the cellulosic biomass solids, and maintaining the catalyst's life represented significant problems to be solved.

As a solution to the foregoing issues, the inventors found that the lignin within the phenolics liquid phase can be at least partially depolymerized in order to reduce the viscosity of this phase. As used herein, the phrases "at least partially depolymerize" and "depolymerize at least a portion of" and grammatical equivalents thereof will be used synonymously with one another. By reducing the viscosity of the phenolics liquid phase, the slurry catalyst was much more readily separable therefrom by liquid-solid separation techniques (e.g., filtration). Once separated, the slurry catalyst could be returned to the cellulosic biomass solids or regenerated, if necessary. Moreover, after depolymerizing the lignin, the slurry catalyst typically exhibited an improved life compared to that seen when lignin depolymerization was not performed. Remaining unbound by any theory or mechanism, it is believed that the phenolics liquid phase coating and/or infiltrating the slurry catalyst may be readily removed from the catalyst particulates once its viscosity is reduced, thereby re-exposing at least some of the catalytic sites. Further, it is believed that removal of the phenolics liquid phase from the pore space of the slurry catalyst may lead to a decreased amount of coking when slurry catalyst regeneration is performed.

Although any suitable technique can be used to affect at least partial depolymerization of the lignin in the phenolics liquid phase, the inventors found hydrotreating to present particular advantages. Specifically, the inventors found that by heating the phenolics liquid phase to a temperature of at least about 250° C. in the presence of molecular hydrogen and a catalyst capable of activating molecular hydrogen, the lignin was sufficiently depolymerized to realize the foregoing advantages. Hydrotreating may beneficially make use of the slurry catalyst that is already accumulated within the phenolics liquid phase. Even more significantly, the above hydrotreating conditions used to affect lignin depolymerization are similar to those used for regenerating catalysts capable of activating molecular hydrogen. Thus, hydrotreating could advantageously be used to dually affect lignin depolymerization and regeneration of the accumulated slurry catalyst. Further advantages of thermally depolymerizing lignin in the manner described above may be realized by coupling the thermal depolymerization process to the process used for further reforming the alcoholic component derived from the cellulosic biomass solids, as described in detail hereinbelow.

As alluded to above, catalyst poisons may be present in cellulosic biomass solids, and the presence of these catalyst poisons as well as other substances may make performing an in situ catalytic reduction reaction process very difficult. In the event that catalyst poisons are not removed from the cellulosic biomass solids prior to commencing hydrothermal digestion, a poison-tolerant catalyst (i.e., a poison-tolerant slurry catalyst that is capable of activating molecular hydrogen) may be used to reduce the frequency of catalyst regeneration and/or replacement. As discussed in more detail hereinafter, sulfided catalysts are one class of poison-tolerant catalysts that may be particularly effective for use in this regard. When processing cellulosic biomass solids via an in situ catalytic reduction reaction process in the presence of a sulfided catalyst, soluble carbohydrates may be converted into an alcoholic component that comprises a high percentage of a glycol. Catalysts that are not poison tolerant may also be used to achieve a similar result, but they may need to be regenerated or replaced more frequently than does a poison-tolerant catalyst. As described hereinafter, the formation of a significant fraction glycols from the cellulosic biomass solids presents both challenges and advantages for further transforming cellulosic biomass solids into fuel blends and other materials.

When processing cellulosic biomass solids, the alcoholic component produced during stabilization of soluble carbohydrates through a catalytic reduction reaction may need to be further reformed in the course of being transformed into more complex organic molecules, particularly those that are suitable for incorporation in fuel blends reminiscent of fossil fuels. In many instances, an initial operation of downstream reforming may comprise a condensation reaction, often conducted in the presence of a condensation catalyst, in which an alcohol or a product formed therefrom is condensed with another molecule to form a higher molecular weight compound. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art. Additional disclosure regarding condensation reactions and catalysts suitable for promoting condensation reactions is provided hereinbelow.

Ordinarily, alcohols do not directly undergo condensation reactions, although they are not expressly precluded from doing so. Instead, in order to undergo a condensation reaction, an alcohol is usually transformed into a carbonyl compound or a compound that may subsequently react to form a carbonyl compound. The transformation to form the carbonyl compound may take place in concert with the condensation reaction or occur in a discrete conversion prior to the condensation reaction. Suitable transformations for converting alcohols into carbonyl compounds or compounds that may be transformed into carbonyl compounds include, for example, dehydrogenation reactions, dehydration reactions, oxidation reactions, or any combination thereof. When the carbonyl compound is formed catalytically, the same catalyst or a different catalyst than that used to carry out the condensation reaction may be used.

Although a number of different types of catalysts may be used for mediating condensation reactions, zeolite catalysts may be particularly advantageous in this regard. One zeolite catalyst that may be particularly well suited for mediating condensation reactions of alcohols is ZSM-5 (Zeolite Socony Mobil 5), a pentasil aluminosilicate zeolite having a composition of $Na_nAl_nSi_{96-n}O_{192}\cdot16H_2O$ (0<n<27), which may transform an alcohol feed into a condensation product. Without being bound by any theory or mechanism, it is believed that this catalyst may promote condensation of alcohols in a concerted manner by mediating a dehydrogenation reaction to produce a carbonyl compound which subsequently undergoes the desired condensation reaction. Other suitable zeolite catalysts may include, for example, ZSM-12, ZSM-22, ZSM-23, SAPO-11, and SAPO-41. Additional types of suitable condensation catalysts are also discussed in more detail herein.

When using zeolite catalysts, it is ordinarily desirable to limit their exposure to water, as the water can incorporate within the zeolite structure and ultimately result in its degradation, particularly under hydrothermal conditions. In addition, when utilizing zeolite catalysts, it is ordinarily desirable to utilize reaction substrates containing only a single alcohol functionality, since more extensively hydroxylated compounds can give rise to undesirable decomposition products due to an increased degree of coking. In light of the foregoing, monohydric alcohols, including monohydric alcohols containing a carbonyl functionality, may be a preferred substrate for condensation reactions mediated by zeolite catalysts. In this regard, monohydric alcohols that are maintained in a water-free or reduced-water state may be particularly desirable. However, monohydric alcohols may be especially difficult to obtain in a reduced-water state, particularly when prepared from biological sources, due to their propensity to form binary azeotropes with water when separating these compounds by distillation, thereby making it difficult to achieve satisfactory drying. Furthermore, the difficulty in removing water from monohydric alcohols by distillation may increase material losses when drying these types of compounds. Accordingly, all other factors being equal, the benefits of lessening the likelihood of catalyst degradation have to be balanced with the difficulties associated with producing a dried monohydric alcohol.

In light of the foregoing, the observed formation of significant glycols during in situ catalytic reduction reaction processes was initially discouraging, given the preferability of monohydric alcohols as a feed for zeolite condensation catalysts. Although the inventors did discover that a glycol could be used successfully as a feed for zeolite condensation catalysts, monohydric alcohols were still found to be superior in this regard. Thus, a separate chemical transformation to produce monohydric alcohols from glycols was deemed desirable.

When producing chemical compounds, conducting additional process operations, particularly additional chemical transformations, is ordinarily considered to be undesirable due to lengthened processing times, increased process complexity, and escalating capital, energy, and labor costs. In contrast to conventional wisdom, however, the present inventors realized that the transformation of soluble carbohydrates into a monohydric alcohol via a glycol intermediate could actually be advantageous. Moreover, the inventors realized that this transformation could be accomplished with little increase in process complexity or cost by coupling the glycol transformation to the thermal treatment of the phenolics liquid phase. Specifically, the inventors determined that by combining the initially produced glycol with the phenolics liquid phase, the glycol could be readily converted into a monohydric alcohol via reduction in the presence of molecular hydrogen and the slurry catalyst. Since these conditions are already present when hydrotreating to reduce the viscosity of the phenolics liquid phase, concurrent reduction of the glycol to a monohydric alcohol does little to increase the process complexity or energy requirements. Once formed, the monohydric alcohol can then be separated from the phenolics liquid phase for further reforming thereafter, if desired.

In addition to the ability to convert the glycol into a monohydric alcohol in an energetically favorable manner, as described above, other significant process advantages may be realized as well. Specifically, in some embodiments, production of a monohydric alcohol via a glycol intermediate may allow the monohydric alcohol to be produced in a reduced-water state much more readily than via direct production from an aqueous phase. Glycols are much less prone to formation of azeotropes with water. Accordingly, glycols can be dried via distillation much more readily and with a lower degree of material loss than can the corresponding monohydric alcohols. Once dried glycols have been produced by distillation or another suitable drying technique, the dried glycols can thereafter be converted via reduction into a monohydric alcohol that maintains a comparable amount of water to the glycol from which it was formed, thereby avoiding the issues noted above.

Although processing a dried glycol in the foregoing manner may result in the advantages noted above, it is to be recognized that the processes described herein may be applicable even when the glycol is not dried and formation of a dried monohydric alcohol is not necessarily desired. For example, the conversion of a glycol into a monohydric alcohol may be realized in a like manner to that described above by combining the phenolics liquid phase and the aqueous phase obtained from hydrothermal digestion of cellulosic biomass solids and thermally treating the resulting mixture. The monohydric alcohol may then be removed from the mixture using a suitable technique for subsequent reforming.

As a further benefit of hydrotreating the phenolics liquid phase, the inventors found that significant quantities of methanol were generated upon heating this phase to a temperature of at least about 250° C. Without being bound by any theory or mechanism, it is believed that the methanol formation occurred due to cleavage of at least some of the phenolic methyl ethers on the lignin polymer backbone. Formation of the methanol represents a significant process advantage, since it comprises a feedstock material that may be transformed into fuel blends and other materials through downstream reforming reactions like those used for further reforming the monohydric alcohol. Thus, methanol generated from the phenolics liquid phase may be combined for further reforming with the glycol or monohydric alcohol generated from the cellulosic biomass solids. Optionally, the methanol may be processed separately or otherwise utilized in some manner. In any event, formation of the methanol advantageously allows a greater weight percentage of the original cellulosic biomass solids to be transformed into useful material.

In addition to methanol, phenolic compounds and other small molecules produced from lignin depolymerization can also be combined with the glycol or monohydric alcohol generated from the cellulosic biomass solids, if desired. Optionally, the phenolic compounds or other small molecules can be processed separately from the glycol or monohydric alcohol. Processing the phenolic compounds and other small molecules in the foregoing manner may again increase the percentage utilization of the starting cellulosic biomass solids and allow custom fuel blends to be made.

Unless otherwise specified, it is to be understood that use of the terms "biomass" or "cellulosic biomass" in the description herein refers to "cellulosic biomass solids." Solids may be in any size, shape, or form. The cellulosic biomass solids may be natively present in any of these solid sizes, shapes, or forms, or they may be further processed prior to hydrothermal digestion. In some embodiments, the cellulosic biomass solids may be chopped, ground, shredded, pulverized, and the like to produce a desired size prior to hydrothermal digestion. In some or other embodiments, the cellulosic biomass solids may be washed (e.g., with water, an acid, a base, combinations thereof, and the like) prior to hydrothermal digestion taking place.

In practicing the present embodiments, any type of suitable cellulosic biomass source may be used. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

Illustrative carbohydrates that may be present in cellulosic biomass solids include, for example, sugars, sugar alcohols, celluloses, lignocelluloses, hemicelluloses, and any combination thereof. Once soluble carbohydrates have been produced through hydrothermal digestion according to the embodiments described herein, the soluble carbohydrates may be transformed into a more stable reaction product predominantly comprising a glycol. As used herein, the term "glycol" will refer to compounds containing two alcohol functional groups, two alcohol functional groups and a carbonyl functionality, or any combination thereof. As used herein, the term "carbonyl functionality" will refer to an aldehyde functionality or a ketone functionality. Although a glycol may comprise a significant fraction of the reaction product, it is to be recognized that other alcohols, including triols and monohydric alcohols, for example, may also be present. Further, any of these alcohols may further include a carbonyl functionality. As used herein, the term "triol" will refer to compounds containing three alcohol functional groups, three alcohol functional groups and a carbonyl functionality, and any combination thereof. As used herein, the term "monohydric alcohol" will refer to compounds containing one alcohol functional group, one alcohol functional group and a carbonyl functionality, and any combination thereof.

As used herein, the term "phenolics liquid phase" will refer to a fluid phase comprising liquefied lignin. In some embodiments, the phenolics liquid phase may be more dense than water, but it may also be less dense than water depending on lignin concentrations and the presence of other components, for example.

As used herein, the term "light organics phase" will refer to a fluid phase that is typically less dense than water and comprises an organic compound. The organic compound may include at least a portion of an alcoholic component formed via catalytic reduction of soluble carbohydrates, which may include $C_4$ or greater alcohols and self-condensation products thereof.

As used herein, the term "dried glycol" refers to a liquid phase comprising a glycol that has had a least a portion of the water removed therefrom. It is to be recognized that a dried glycol need not necessarily be completely anhydrous when dried, simply that its water content be reduced (e.g., less than 50 wt. % water). In some embodiments, the dried glycol may comprise about 40 wt. % or less water. In some or other embodiments, the dried glycol may comprise about 35 wt. % or less water, or about 30 wt. % or less water, or about 25 wt. % or less water, or about 20 wt. % or less water, or about 15 wt. % or less water, or about 10 wt. % or less water, or about 5 wt. % or less water. In some embodiments of the methods described herein, a substantially anhydrous glycol may be produced upon drying the reaction product. As used herein, a substance will be considered to be substantially anhydrous if it contains about 5 wt. % water or less.

In some embodiments, methods described herein can comprise: providing cellulosic biomass solids in the presence of a digestion solvent, molecular hydrogen, and a slurry catalyst capable of activating molecular hydrogen; at least partially converting the cellulosic biomass solids into a phenolics liquid phase comprising lignin, an aqueous phase comprising a glycol derived from the cellulosic biomass solids, and an optional light organics phase; wherein at least a portion of the slurry catalyst accumulates in the phenolics liquid phase as it forms; combining the glycol with the phenolics liquid phase, thereby forming a combined phase; and heating the combined phase in the presence of molecular hydrogen; wherein heating the combined phase reduces the viscosity of the phenolics liquid phase and transforms at least a portion of the glycol into a monohydric alcohol.

In some embodiments, the glycol may be formed by a catalytic reduction reaction of soluble carbohydrates, where the soluble carbohydrates are derived from the cellulosic biomass solids. Cellulosic biomass contains approximately 50% water by weight, and approximately 30% of the dry portion comprises lignin biopolymer. Accordingly, cellulosic biomass solids contain up to about 35 percent by weight cellulosic material (70% cellulosic material by weight on a dry basis) that can be converted into soluble carbohydrates and products derived therefrom, including glycols. In some embodiments, at least about 5 percent by weight of the cellulosic biomass solids may be converted into a glycol. In other embodiments, at least about 10 percent by weight of the cellulosic biomass solids may be converted into a glycol. In some embodiments, between about 5% and about 35% of the cellulosic biomass solids by weight may be converted into a glycol, or between about 10% and about 30% of the cellulosic biomass solids by weight, or between about 5% and about 25% of the cellulosic biomass solids by weight, or between about 5% and about 20% of the cellulosic biomass solids by weight, or between about 5% and about 15% of the cellulosic biomass solids by weight, or between about 10% and about 25% of the cellulosic biomass solids by weight, or between about 10% and about 20% of the cellulosic biomass solids by weight, or between about 10% and about 15% of the cellulosic biomass solids by weight. Separation and recycle of the glycol may be used to increase the glycol content of the digestion solvent. For example, in some embodiments, the digestion solvent may comprise between about 10% glycol and about 90% glycol by weight.

In some embodiments, the glycol may be formed in a hydrothermal digestion unit via an in situ catalytic reduction reaction process, as described above. Although a glycol may be formed via an in situ catalytic reduction reaction process, it is to be recognized that, in alternative embodiments, a glycol may also be formed without conducting the digestion of cellulosic biomass solids in the presence of molecular hydrogen and a slurry catalyst capable of activating molecular hydrogen. For example, in some embodiments, soluble carbohydrates may be produced in a liquor phase in a hydrothermal digestion unit, and the liquor phase may be transferred to a separate reactor unit for conversion into a glycol, thereby achieving a like result. In such an approach, the catalyst in the separate reactor unit need not necessarily comprise a slurry catalyst, although it is not precluded from being so. For example, the catalyst in the separate reactor unit may be capable of activating molecular hydrogen and include one or more catalyst forms such as, for example, slurry catalysts, fixed bed catalysts, ebullating bed catalysts, and the like. Thus, in some embodiments, a phenolics liquid phase may be formed in a separate reactor unit, and a slurry catalyst may be added to the phenolics liquid phase after its formation to achieve a like result to that obtained when a slurry catalyst accumulates directly in the phenolics liquid phase by an in situ catalytic reduction process. Further, in some embodiments, additional slurry catalyst may be added to the phenolics liquid phase to supplement the amount that accumulates therein during formation of the phenolics liquid phase. For example, in some embodiments, addition of a supplemental quantity of the slurry catalyst to the phenolics liquid phase may be desirable to achieve a satisfactory conversion of the glycol into a monohydric alcohol and/or to reduce the viscosity of the phenolics liquid phase to a desired degree during hydrotreating.

In some embodiments, the catalytic reduction reaction used to produce the glycol may take place at a temperature ranging between about 110° C. and about 300° C., or between about 170° C. and about 300° C., or between about 180° C. and about 290° C., or between about 150° C. and about 250° C. In some embodiments, the catalytic reduction reaction may take place at a pH ranging between about 7 and about 13, or between about 10 and about 12. In other embodiments, the catalytic reduction reaction may take place under acidic conditions, such as a pH of about 5 to about 7. In some embodiments, the catalytic reduction reaction may be conducted under a hydrogen partial pressure ranging between about 1 bar (absolute) and about 150 bar, or between about 15 bar and about 140 bar, or between about 30 bar and about 130 bar, or between about 50 bar and about 110 bar.

In various embodiments, the digestion solvent in which soluble carbohydrates are formed from cellulosic biomass solids and converted into a glycol may comprise an organic solvent. In various embodiments, the digestion solvent may comprise an organic solvent and water. Although any organic solvent that is at least partially miscible with water may be used in the digestion solvent, particularly advantageous organic solvents are those that can be directly converted into fuel blends and other materials without being separated from the glycol. That is, particularly advantageous organic solvents are those that may be co-processed along with the glycol during downstream reforming reactions into fuel blends and other materials. Suitable organic solvents in this regard may include, for example, ethanol, ethylene glycol, propylene glycol, glycerol, and any combination thereof.

In some embodiments, the digestion solvent may further comprise a small amount of a monohydric alcohol. The presence of at least some monohydric alcohols in the digestion solvent may desirably enhance the hydrothermal digestion and/or the catalytic reduction reactions being conducted therein. For example, inclusion of about 1% to about 5% by weight monohydric alcohols in the digestion solvent may desirably maintain catalyst activity due to a surface cleaning effect. At higher concentrations of monohydric alcohols, bulk solvent effects may begin to predominate. In some embodiments, the digestion solvent may comprise about 10 wt. % or less monohydric alcohols, with the balance of the digestion solvent comprising water and another organic solvent. In some embodiments, the digestion solvent may comprise about 5 wt. % or less monohydric alcohols, or about 4% or less monohydric alcohols, or about 3% or less monohydric alcohols, or about 2% of less monohydric alcohols, or about 1% or less monohydric alcohols. Monohydric alcohols present in the digestion solvent may arise from any source. In some embodiments, the monohydric alcohols may be formed as a co-product with the glycols being formed by the catalytic reduction reaction. In some or other embodiments, the monohydric alcohols may be formed by heating of the combined phase in the presence of molecular hydrogen and thereafter returned to the cellulosic biomass solids. In still other embodiments, the monohydric alcohols may be sourced from an external feed that is in flow communication with the cellulosic biomass solids.

In some embodiments, the digestion solvent may comprise between about 1% water and about 99% water, with the organic solvent comprising the balance of the digestion solvent composition. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the digestion solvent may comprise about 90% or less water by weight. In other embodiments, the digestion solvent may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

As described above, the viscosity of the phenolics liquid phase may increase as it forms, eventually making it difficult to process this phase and/or remove the slurry catalyst that accumulates therein. In addition, the activity of the slurry catalyst may also decrease as the phenolics liquid phase forms. To address the foregoing issues, the lignin may be at least partially depolymerized to promote a decrease in the viscosity of the phenolics liquid phase. In some embodiments, heating the combined phase in the presence of molecular hydrogen may at least partially depolymerize the lignin present therein. The lignin within the combined phase need not necessarily be completely depolymerized to achieve a beneficial reduction in viscosity. In some embodiments, the viscosity may be reduced by at most about 20% by at least partially depolymerizing the lignin. In some or other embodiments, the viscosity may be reduced by at most about 15%, or by at most about 10%, or by at most about 5% by at least partially depolymerizing the lignin. In some embodiments, the viscosity may be reduced such that it does not exceed a desired level (e.g., about 1000 cP).

In some embodiments, the cellulosic biomass solids may be heated to a first temperature to form the phenolics liquid phase and the aqueous phase, and the combined phase may be heated to a second temperature to at least partially depolymerize the lignin present therein. In some embodiments, the first temperature may be lower than the second temperature. In some embodiments, the first temperature may be insufficient to at least partially depolymerize the lignin. That is, in such embodiments, the phenolics liquid phase may be formed at a first temperature without depolymerizing the lignin, and the combined phase may then be formed and heated to the second temperature that at least partially depolymerizes the lignin and converts the glycol into a monohydric alcohol. In alternative embodiments, both the first and second temperatures may be sufficient to at least partially depolymerize the lignin. When the present methods are practiced in such a manner, continued depolymerization of the lignin may occur while forming the monohydric alcohol from the glycol.

Although formation of the phenolics liquid phase may take place over a range of temperatures, as described above, it is believed that it may be desirable to form this phase at as low a temperature as possible. Lower temperatures may help maintain the reaction product formed from cellulosic biomass solids at a glycol state without forming excessive amounts of a monohydric alcohol. If excessive quantities of monohydric alcohol were to be formed before at least partial drying of the aqueous phase takes place, some of the particular benefits associated with the present methods would be lost. Specifically, the ability to produce a dried monohydric alcohol from the combined phase would be decreased. In addition to the foregoing benefits, use of lower reaction temperatures may be desirable from an energy efficiency standpoint.

In some embodiments, heating to form the phenolics liquid phase may take place at a first temperature of about 250° C. or lower. In some embodiments, heating to form the phenolics liquid phase may take place at a first temperature of about 240° C. or lower, or about 230° C. or lower, or about 220° C. or lower, or about 210° C. or lower, or about 200° C. or lower. In some embodiments, heating to form the phenolics liquid phase may take place at a first temperature ranging between about 150° C. and about 250° C. In some embodiments, heating to form the phenolics liquid phase may take place at a first temperature ranging between about 160° C. and about 240° C., or between about 170° C. and about 230° C., or between about 180° C. and about 220° C., or between about 200° C. and about 250° C., or between about 200° C. and about 240° C., or between about 200° C. and about 230° C., or between about 210° C. and about 250° C., or between about 210° C. and about 240° C., or between about 210° C. and about 230° C., or between about 220° C. and about 250° C., or between about 220° C. and about 240° C.

In some embodiments, heating the combined phase may take place at a second temperature of about 250° C. or higher. More specifically, in some embodiments, heating to reduce the viscosity of the phenolics liquid phase may take place at a temperature that is sufficient to at least partially depolymerize the lignin therein. In some embodiments, heating the combined phase may take place at a second temperature of at least about 260° C., or of at least about 265° C., or of at least about 270° C., or at least about 275° C., or at least about 280° C., or at least about 285° C., or at least about 290° C., or at least about 295° C., or at least about 300° C. In some embodiments, heating the combined phase may take place at a second temperature ranging between about 250° C. and about 330° C., or between about 260° C. and about 320° C., or between about 270° C. and about 300° C., or between about 250° C. and about 300° C., or between about 260° C. and about 290° C., or between about 270° C. and about 290° C. As one of ordinary skill in the art will recognize, the vapor pressure of the combined phase will increase as the temperature increases. Thus, at least to some degree, suitable operating temperatures for heating the combined phase may be constrained by the presence of extraneous solvents and/or water that may also be present in the combined phase and result in excessive vapor pressure increases. In this regard, safe operating pressure ranges for the vessel in which the combined phase is heated may also need to be considered.

In some embodiments, heating of the cellulosic biomass solids and the digestion solvent to form soluble carbohydrates and a phenolics liquid phase may take place while the cellulosic biomass solids are in a pressurized state. As used herein, the term "pressurized state" refers to a pressure that is greater than atmospheric pressure (1 bar). Heating a digestion solvent in a pressurized state may allow the normal boiling point of the digestion solvent to be exceeded, thereby allowing the rate of hydrothermal digestion to be increased relative to lower temperature digestion processes. In some embodiments, heating the cellulosic biomass solids and the digestion solvent may take place at a pressure of at least about 30 bar. In some embodiments, heating the cellulosic biomass solids and the digestion solvent may take place at a pressure of at least about 60 bar, or at a pressure of at least about 90 bar. In some embodiments, heating the cellulosic biomass solids and the digestion solvent may take place at a pressure ranging between about 30 bar and about 430 bar. In some embodiments, heating the cellulosic biomass solids and the digestion solvent may take place at a pressure ranging between about 50 bar and about 330 bar, or at a pressure ranging between about 70 bar and about 130 bar, or at a pressure ranging between about 30 bar and about 130 bar.

In some embodiments, methods described herein may further comprise measuring the viscosity of the phenolics liquid phase, and heating the combined phase until a desired viscosity has been reached. Any technique for measuring viscosity may be used in conjunction with the methods described herein. Suitable instrumental techniques for measuring viscosity will be familiar to one having ordinary skill in the art and may include, for example, viscometry and rheometry. In some embodiments, heating of the combined phase may occur until a pre-determined viscosity has been attained. In some embodiments, heating of the combined phase may occur until the viscosity has been reduced by a fixed percentage. In some or other embodiments, heating of the combined phase may take place until the viscosity has been decreased sufficiently for the slurry catalyst to be removed therefrom. In still other embodiments, heating of the combined phase may take place until the viscosity has decreased sufficiently for the phenolics liquid phase and/or the combined phase to be effectively transferred or otherwise processed. The choice of a suitable viscosity may be a matter of operational constraints and may not be the same in all cases. Given the benefit of the present disclosure, one of ordinary skill in the art will be able to determine a viscosity appropriate for use in a given application.

In addition to at least partially depolymerizing the lignin in the combined phase at the second temperature, the slurry catalyst may, in some embodiments, also be at least partially regenerated while heating the combined phase to the second temperature in the presence of molecular hydrogen. In some embodiments, methods described herein may further comprise separating the slurry catalyst from the combined phase after reducing the viscosity (i.e., after heating to the second temperature). After viscosity reduction, removal of the slurry catalyst from the combined phase may take place by any technique known to one having ordinary skill in the art. Suitable techniques may include, for example, filtration, centrifugation, hydroclone separation, gravity settling, any combination thereof, and the like.

In some embodiments, the methods may further comprise returning the slurry catalyst to the cellulosic biomass solids so as to maintain the ongoing catalytic reduction reaction. In some embodiments, the slurry catalyst may be returned directly to the cellulosic biomass solids after being removed from the combined phase. In some or other embodiments, the slurry catalyst may be further regenerated before being returned to the cellulosic biomass solids. Further regeneration of the slurry catalyst may be desirable if its catalytic activity is not sufficiently high, for example. Return of the slurry catalyst to the cellulosic biomass solids may occur continuously or non-continuously (e.g., in batch mode). In some embodiments, fluid flow may be used to return the slurry catalyst to the cellulosic biomass solids. For example, in various embodiments, the slurry catalyst may be carried by a stream of the digestion solvent, a recycle stream of the aqueous phase, a recycle stream of the separated glycol or monohydric alcohol, or any combination thereof to return the slurry catalyst to the cellulosic biomass solids.

In some embodiments, methods described herein may further comprise separating the phenolics liquid phase from the cellulosic biomass solids. In some embodiments, the phenolics liquid phase may be separated from the cellulosic biomass solids before combining the glycol with the phenolics liquid phase. For example, in some embodiments, combining a dried glycol with the phenolics liquid phase may take place after separation of the phenolics liquids phase from the cellulosic biomass solids. However, in some embodiments, the glycol may be combined with the phenolics liquid phase while still in contact with the cellulosic biomass solids.

In some embodiments, the glycol may be combined with the phenolics liquids phase without the glycol having been at least partially dried. That is, in some embodiments, the aqueous phase and the phenolics liquids phase may be combined with one another and the glycol therein may then be at least partially converted into a monohydric alcohol while heating the combined phase. As discussed above, when the glycol is not at least partially dried prior to being converted into a monohydric alcohol, certain process advantages described herein may not be realized. Suitable techniques for combining the phenolics liquid phase and the aqueous phase with one another may include, for example, co-circulation of the two phases, treating at least one of the phases with a surfactant, mechanically agitating the phases to produce an emulsion, jet mixing, and the like. Techniques for thermally treating a combined phase comprising a phenolics liquid phase and an aqueous phase are described in commonly owned U.S. Patent Application 61/720,747 entitled "Methods and Systems For Processing Lignin During Hydrothermal Digestion of Cellulosic Biomass Solids," filed Oct. 31, 2012 and incorporated by reference in its entirety.

In some embodiments, the glycol may be at least partially separated from the aqueous phase prior to being combined with the phenolics liquid phase. That is, in some embodiments, methods described herein may further comprise removing at least a portion of the water from the aqueous phase, thereby producing a dried glycol. In such embodiments, the dried glycol may be combined with the phenolics liquid phase to form the combined phase for processing by the techniques described herein. As discussed above, such an approach may allow certain process advantages to be realized. Specifically, the monohydric alcohol formed from the dried glycol may contain a comparable amount of water as the glycol from which it was formed, thereby decreasing hydrothermal stress on a zeolite condensation catalyst during downstream reforming. In more particular embodiments, methods described herein may further comprise separating the phenolics liquid phase from the aqueous phase, and after separating the phenolics liquid phase from the aqueous phase, removing at least a portion of the water from the aqueous phase, thereby producing a dried glycol. Again, the dried glycol can be combined with the phenolics liquid phase for processing by the techniques described herein.

The technique by which at least a portion of the water is removed from the aqueous phase to produce a dried glycol is not believed to be particularly limited. In some embodiments, removing at least a portion of the water from the aqueous phase may comprise a distillation to separate at least a portion of the water from the glycol. Water present in the aqueous phase may arise from any source including, for example, the digestion solvent used to conduct hydrothermal digestion, the cellulosic biomass itself, and the catalytic reduction reaction(s) performed in conjunction with stabilizing soluble carbohydrates (e.g., as a product of a hydrogenolysis and/or hydrogenation reaction). In general, glycols have higher boiling points than that of the water being separated from the glycols. For example, ethylene glycol, the smallest glycol, has a boiling point of 197° C., and propylene glycol, has a boiling point of 188° C., each of which is much higher than water's 100° C. boiling point, thereby permitting ready removal of at least a portion of the water by distillation techniques to leave behind dried glycols having a decreased water content. Optionally, the dried glycols may be volatilized by distillation and isolated following the initial removal of water. In other embodiments, the dried glycols remaining in the distillation bottoms may be used directly following removal of water by distillation. It is to be recognized that other techniques for water removal may be used instead of or in combination with distillation techniques to separate water from the glycol in the aqueous phase. For example, in some embodiments, the glycol may be separated from the aqueous phase by solvent extraction and dried thereafter. In some or other embodiments, the solvent extract containing the glycol may be contacted with a bed of a drying agent such as an anhydrous inorganic salt, molecular sieves, silica gel, alumina, or the like to affect the removal of at least a portion of the water therefrom. In some embodiments, a glycol that has been at least partially dried by distillation may be further dried through contact with a drying agent. In alternative embodiments, the aqueous phase may be contacted directly with a drying agent to affect removal of at least a portion of the water present therein.

In some embodiments, methods described herein may further comprise separating at least a portion of the phenolics liquid phase from the cellulosic biomass solids and then returning at least a portion of the phenolics liquid phase or the combined phase to the cellulosic biomass solids. For example, in some embodiments, at least a portion of the phenolics liquid phase or the combined phase may be circulated external to the cellulosic biomass solids and thereafter returned thereto. Optionally, at least partial lignin depolymerization may occur during circulation. In some or other embodiments, at least a portion of the phenolics liquid phase or the combined phase may be conveyed to a point above at least a portion of the cellulosic biomass solids and released, thereby releasing the slurry catalyst for downward percolation through the cellulosic biomass solids. Techniques for downward percolation of a slurry catalyst through cellulosic biomass solids using a phenolics liquid phase are described in commonly owned U.S. Patent Application 61/720,757, entitled "Methods and Systems for Distributing a Slurry Catalyst in Cellulosic Biomass Solids," filed Oct. 31, 2012 and incorporated herein by reference in its entirety. In other embodiments described herein, the phenolics liquid phase, once removed from the cellulosic biomass solids, is not returned thereto.

In some embodiments, at least a portion of the phenolics liquid phase or the combined phase may be returned to the cellulosic biomass solids once at least partial lignin depolymerization has occurred. In other embodiments, the phenolics liquid phase or the combined phase may remain separated from the cellulosic biomass solids and undergo further processing thereafter. For example, in some embodiments, the slurry catalyst within the phenolics liquid phase or the combined phase may be separated therefrom, and/or the compounds generated from partial lignin depolymerization may be further processed, if desired.

In some embodiments, catalysts capable of activating molecular hydrogen and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst capable of activating molecular hydrogen may be deposited on a catalyst support that is not itself catalytically active.

In some embodiments, the catalyst that is capable of activating molecular hydrogen may comprise a slurry catalyst. In some embodiments, the slurry catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom. Catalysts that are not poison tolerant may also be used to achieve a similar result, but they may need to be regenerated or replaced more frequently than does a poison-tolerant catalyst.

In some embodiments, suitable poison-tolerant catalysts may include, for example, sulfided catalysts. In some or other embodiments, nitrided catalysts may be used as poison-tolerant catalysts. Sulfided catalysts suitable for activating molecular hydrogen are described in commonly owned United States Patent Application Publications 2013/0109896, and 2012//0317872 each of which is incorporated herein by reference in its entirety. Sulfiding may take place by treating the catalyst with hydrogen sulfide or an alternative sulfiding agent, optionally while the catalyst is disposed on a solid support. In more particular embodiments, the poison-tolerant catalyst may comprise a sulfided cobalt-molybdate catalyst, such as a catalyst comprising about 1-10 wt. % cobalt oxide and up to about 30 wt. % molybdenum trioxide. In other embodiments, catalysts containing Pt or Pd may also be effective poison-tolerant catalysts for use in the techniques described herein. When mediating in situ catalytic reduction reaction processes, sulfided catalysts may be particularly well suited to form reaction products comprising a substantial fraction of glycols (e.g., $C_2$-$C_6$ glycols) without producing excessive amounts of the corresponding monohydric alcohols. Although poison-tolerant catalysts, particularly sulfided catalysts, may be well suited for forming glycols from soluble carbohydrates, it is to be recognized that other types of catalysts, which may not necessarily be poison-tolerant, may also be used to achieve a like result in alternative embodiments. As will be recognized by one having ordinary skill in the art, various reaction parameters (e.g., temperature, pressure, catalyst composition, introduction of other components, and the like) may be modified to favor the formation of a desired reaction product. Given the benefit of the present disclosure, one having ordinary skill in the art will be able to alter various reaction parameters to change the product distribution obtained from a particular catalyst and set of reactants.

In some embodiments, slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like. In some embodiments, the slurry catalyst may be concentrated in the fluid phase after sulfiding, and the concentrated slurry may then be distributed in the cellulosic biomass solids using fluid flow. Illustrative techniques for catalyst sulfiding that may be used in conjunction with the methods described herein are described in United States Patent Application Publication No. 20100236988 and incorporated herein by reference in its entirety.

In various embodiments, slurry catalysts used in conjunction with the methods described herein may have a particulate size of about 250 microns or less. In some embodiments, the slurry catalyst may have a particulate size of about 100 microns or less, or about 10 microns or less. In some embodiments, the minimum particulate size of the slurry catalyst may be about 1 micron. In some embodiments, the slurry catalyst may comprise catalyst fines in the processes described herein. As used herein, the term "catalyst fines" refers to solid catalysts having a nominal particulate size of about 100 microns or less. Catalyst fines may be generated from catalyst production processes, for example, during extrusion of solid catalysts. Catalyst fines may also be produced by grinding larger catalyst solids or during regeneration of catalyst solids. Suitable methods for producing catalyst fines are described in U.S. Pat. Nos. 6,030,915 and 6,127,229, each of which is incorporated herein by reference in its entirety. In some instances, catalyst fines may be intentionally removed from a solid catalyst production run, since they may be difficult to sequester in some catalytic processes. Techniques for removing catalyst fines from larger catalyst solids may include, for example, sieving or like size separation processes. When conducting in situ catalytic reduction reaction processes, such as those described herein, catalyst fines may be particularly well suited, since they can be easily fluidized and distributed in the interstitial pore space of the digesting cellulosic biomass solids.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

In some embodiments, the catalysts used in conjunction with the processes described herein may be operable to generate molecular hydrogen. For example, in some embodiments, catalysts suitable for aqueous phase reforming (i.e., APR catalysts) may be used. Suitable APR catalysts may include, for example, catalysts comprising Pt, Pd, Ru, Ni, Co, or other Group VIII metals alloyed or modified with Re, Mo, Sn, or other metals. Thus, in some embodiments described herein, an external hydrogen feed may not be needed in order to effectively carry out the stabilization of soluble carbohydrates by a catalytic reduction reaction. However, in other embodiments, an external hydrogen feed may be used, optionally in combination with internally generated hydrogen.

In some embodiments, the molecular hydrogen may be externally supplied to the cellulosic biomass solids. For example, in some embodiments, the molecular hydrogen may be supplied as an upwardly directed fluid stream. Benefits of supplying an upwardly directed fluid stream have been described herein. In some or other embodiments, the molecular hydrogen may be generated internally through use of an APR catalyst.

In various embodiments described herein, a slurry catalyst may be at least partially distributed within a charge of cellulosic biomass solids, particularly using upwardly directed fluid flow. As used herein, the terms "distribute," "distribution," and variants thereof refer to a condition in which a slurry catalyst is present at all heights of a charge of cellulosic biomass. No particular degree of distribution is implied by use of the term "distribute" or its variants. In some embodiments, the distribution may comprise a substantially homogeneous distribution, such that a concentration of the slurry catalyst is substantially the same at all heights of a cellulosic biomass charge. In other embodiments, the distribution may comprise a heterogeneous distribution, such that different concentrations of the slurry catalyst are present at various heights of the cellulosic biomass charge. When a heterogeneous distribution of the slurry catalyst is present, a concentration of the slurry catalyst within the cellulosic biomass solids may increase from top to bottom in some embodiments or decrease from top to bottom in other embodiments. In some embodiments, a heterogeneous distribution may comprise an irregular concentration gradient.

In some embodiments, the methods described herein may further comprise supplying upwardly directed fluid flow through the cellulosic biomass solids. In various embodiments, the upwardly directed fluid flow may comprise a gas stream, a liquid stream, or any combination thereof. In some embodiments, the upwardly directed fluid flow may comprise one upwardly directed fluid stream, or two upwardly directed fluid streams, or three upwardly directed fluid streams, or four upwardly directed fluid streams, or five upwardly directed fluid streams.

In some embodiments, at least some of the one or more upwardly directed fluid streams may contain the slurry catalyst at its source. That is, the fluid stream(s) may comprise a stream of the slurry catalyst. The one or more upwardly directed fluid streams may convey the slurry catalyst therein, thereby at least partially distributing the slurry catalyst in the cellulosic biomass solids. In some embodiments, the upwardly directed fluid stream may comprise a circulating liquid containing the slurry catalyst therein. In other embodiments, the one or more upwardly directed fluid streams may not contain the slurry catalyst at its source, but they may still fluidize slurry catalyst located in or near the cellulosic biomass solids. For example, a gas stream may not contain the slurry catalyst at its source, but it may still promote fluidization of slurry catalyst in or near the cellulosic biomass solids. A liquid stream lacking the slurry catalyst may promote fluidization of slurry catalyst in or near the cellulosic biomass solids in a manner like that described for a gas stream.

In some embodiments, the one or more upwardly directed fluid streams may comprise a gas stream. For example, in some embodiments, a gas stream being used for upwardly directed fluid flow may comprise a stream of molecular hydrogen. In some or other embodiments, steam, compressed air, or an inert gas such as nitrogen, for example, may be used in place of or in addition to a stream of molecular hydrogen.

Up to about 40% steam may be present in the fluid stream in various embodiments. An upwardly directed gas stream may be used to distribute the slurry catalyst within the cellulosic biomass solids when a liquid stream alone is insufficient to distribute the slurry catalyst, for example. When used alone, a gas stream generally does not convey the slurry catalyst beyond a liquid head surrounding the cellulosic biomass solids. That is, a gas stream used alone does not convey the slurry catalyst beyond the aqueous phase and/or optional light organics phase disposed about the cellulosic biomass solids.

In some embodiments, the one or more upwardly directed fluid streams may comprise a liquid stream. An upwardly directed liquid stream may be used to distribute the slurry catalyst within the cellulosic biomass solids when it is not necessarily desired to maintain the slurry catalyst within the cellulosic biomass solids and/or a gas stream alone is insufficient to distribute the slurry catalyst, for example. Unlike a gas stream, described above, a liquid stream may, in some embodiments, convey the slurry catalyst through the cellulosic biomass solids, add to the liquid head surrounding the cellulosic biomass solids, and eventually spill over. In other embodiments, slurry catalyst fluidization may be incomplete, and a liquid stream may still not convey the slurry catalyst completely through the cellulosic biomass solids before the liquid head spills over.

In some embodiments, at least a portion of the liquid head disposed about the cellulosic biomass solids may be circulated through the cellulosic biomass solids. As used herein, the term "circulate" and variants thereof will be used to refer to the condition that exists when at least a portion of the liquid head (e.g., the aqueous phase or another liquid phase) is removed from the cellulosic biomass solids and is subsequently reintroduced one or more times thereto. The liquid head may comprise the digestion solvent, any liquid phase being added by a liquid stream, and any liquid component being formed from the cellulosic biomass solids. More specifically, the liquid head may comprise the phenolics liquid phase, the aqueous phase, the optional light organics phase, any liquid phase being added by a liquid stream, and/or any liquid component being formed from the cellulosic biomass solids. In some embodiments, the aqueous phase may be maintained with the cellulosic biomass solids by circulating at least a portion of the aqueous phase through the cellulosic biomass solids. In some embodiments, at least a portion of the slurry catalyst may circulate with the aqueous phase through the cellulosic biomass solids. In some or other embodiments, circulation of the aqueous phase may promote fluidization of the slurry catalyst in the cellulosic biomass solids such that the slurry catalyst accumulates in the phenolics liquid phase less rapidly. In still other embodiments, circulation of the aqueous phase may pass through the phenolics liquid phase such that slurry catalyst accumulated therein is at least partially fluidized for distribution in the cellulosic biomass solids. In some embodiments, at least one phase may be circulated through the cellulosic biomass solids such that upwardly directed fluid flow is supplied therethrough.

In some embodiments, methods described herein can comprise: providing cellulosic biomass solids in the presence of a digestion solvent, molecular hydrogen, and a slurry catalyst capable of activating molecular hydrogen; heating the cellulosic biomass solids to a first temperature and forming a phenolics liquid phase comprising lignin, an aqueous phase comprising a glycol derived from the cellulosic biomass solids, and an optional light organics phase; wherein at least a portion of the slurry catalyst accumulates in the phenolics liquid phase as it forms; separating the phenolics liquid phase from the aqueous phase and the cellulosic biomass solids; removing at least a portion of the water from the aqueous phase, thereby producing a dried glycol; combining the dried glycol with the phenolics liquid phase, thereby forming a combined phase; and heating the combined phase to a second temperature in the presence of molecular hydrogen, the second temperature being sufficient to reduce the viscosity of the phenolics liquid phase and transform at least a portion of the dried glycol into a monohydric alcohol; wherein the first temperature is lower than the second temperature.

In some embodiments, a hydrothermal digestion unit in which digestion of the cellulosic biomass solids is taking place may be charged with a fixed amount of slurry catalyst, while cellulosic biomass solids are continuously or semi-continuously fed thereto, thereby allowing hydrothermal digestion to take place in a continual manner. That is, fresh cellulosic biomass solids may be added to the hydrothermal digestion unit on an ongoing basis or an as-needed basis in order to replenish cellulosic biomass solids that have been digested to form soluble carbohydrates. As noted above, ongoing addition of cellulosic biomass solids may result in formation of the phenolics liquids phase. In some embodiments, the cellulosic biomass solids may be continuously or semi-continuously added to the hydrothermal digestion unit while the hydrothermal digestion unit is in a pressurized state. In some embodiments, the pressurized state may comprise a pressure of at least about 30 bar. Without the ability to introduce fresh cellulosic biomass solids to a pressurized hydrothermal digestion unit, depressurization and cooling of the hydrothermal digestion unit may take place during biomass addition, significantly reducing the energy- and cost-efficiency of the biomass conversion process. As used herein, the term "continuous addition" and grammatical equivalents thereof will refer to a process in which cellulosic biomass solids are added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of cellulosic biomass solids to a hydrothermal digestion unit without fully depressurizing the hydrothermal digestion unit. Techniques through which cellulosic biomass solids may be added continuously or semi-continuously to a pressurized hydrothermal digestion unit are discussed in more detail hereinbelow.

In some embodiments, cellulosic biomass solids being continuously or semi-continuously added to the hydrothermal digestion unit may be pressurized before being added to the hydrothermal digestion unit, particularly when the hydrothermal digestion unit is in a pressurized state. Pressurization of the cellulosic biomass solids from atmospheric pressure to a pressurized state may take place in one or more pressurization zones before addition of the cellulosic biomass solids to the hydrothermal digestion unit. Suitable pressurization zones that may be used for pressurizing and introducing cellulosic biomass solids to a pressurized hydrothermal digestion unit are described in more detail in commonly owned United States Patent Application Publications 2013/0152457 and 2013/0152458, and incorporated herein by reference in its entirety. Suitable pressurization zones described therein may include, for example, pressure vessels, pressurized screw feeders, and the like. In some embodiments, multiple pressurization zones may be connected in series to increase the pressure of the cellulosic biomass solids in a stepwise manner.

In some embodiments, at least a portion of the glycol or the monohydric alcohol formed therefrom may be returned to the cellulosic biomass solids after at least a portion of the water has been removed from the aqueous phase. Return of a dried glycol or dried monohydric alcohol may be used to reduce the water content of the digestion solvent, if desired, thereby promoting solubility of soluble carbohydrates and facilitating the removal of deposits from the slurry catalyst, for example. As described hereinafter, monohydric alcohols not being returned to the cellulosic biomass solids may be subjected to further reforming reactions.

In some embodiments, methods described herein may further comprise separating the monohydric alcohol from the combined phase. Separation of the monohydric alcohol may take place by any technique known to one having ordinary skill in the art. Illustrative separation techniques may include, for example, distillation, solvent extraction, any combination thereof, and the like. In some embodiments, the monohydric alcohol may be distilled from the combined phase as it is being heated to reduce the viscosity. In some or other embodiments, distillation of the monohydric alcohol to separate it from the combined phase may take place after viscosity reduction takes place.

As described above, another desirable feature of the methods described herein is that methanol may be formed from the lignin while heating the combined phase. Methanol production from the lignin may increase the percentage of the original cellulosic biomass solids that are converted into useful materials. In some embodiments, methods described herein may further comprise separating the methanol from the combined phase. Separation of the methanol may take place using any of the techniques described above for separating the monohydric alcohol from the combined phase. In some embodiments, the methanol may be separated from the combined phase separately from the monohydric alcohol. In some or other embodiments, the methanol and the monohydric alcohol may be separated together from the combined phase. After separation from the combined phase, the monohydric alcohol and/or the methanol may be further reformed, as described hereinafter. For example, in some embodiments, the monohydric alcohol and/or the methanol or a product derived therefrom may undergo a condensation reaction. In some embodiments, the methanol and the monohydric alcohol may be subsequently reformed together, while in other embodiments, they may be reformed separately. Moreover, the methanol and/or the monohydric alcohol may be subsequently reformed with the light organics phase, or the light organics phase may be further processed separately.

In some embodiments, after reducing the viscosity and separating the slurry catalyst from the combined phase, the phenolics liquid phase may be still further processed. In some embodiments, reaction products resulting from lignin depolymerization (e.g., phenolic compounds and/or methanol) may be separated from the combined phase and further processed. The reaction products resulting from lignin depolymerization may be processed separately from the monohydric alcohol produced as described above, or the reaction products resulting from lignin depolymerization may be combined with the monohydric alcohol and further reformed. By combining the reaction products resulting from lignin depolymerization with the monohydric alcohol, different fuel blends may be produced than can be obtained through further reforming of the monohydric alcohol alone.

In some embodiments, the monohydric alcohol produced from the glycol may be further reformed through any combination and sequence of further hydrogenolysis reactions and/or hydrogenation reactions, condensation reactions, isomerization reactions, oligomerization reactions, hydrotreating reactions, alkylation reactions, dehydration reactions, desulfurization reactions, and the like. The subsequent reforming reactions may be catalytic or non-catalytic. In some embodiments, an initial operation of downstream reforming may comprise a condensation reaction, often conducted in the presence of a condensation catalyst, in which the monohydric alcohol or a product formed therefrom is condensed with another molecule to form a higher molecular weight compound. Additional disclosure regarding condensation reactions and catalysts suitable for promoting condensation reactions is provided hereinbelow.

In some embodiments, prior to performing a condensation reaction, a slurry catalyst used in conjunction with mediating the formation of the glycol may be removed from the combined phase. Suitable techniques for removing a slurry catalyst from the combined phase may include, for example, filtration, membrane separation, separation by centrifugal or centripetal force (e.g., hydroclones and centrifuges), gravity-induced settling, and the like. In some embodiments, slurry catalyst may remain as a bottoms residue when distillation is used to separate the monohydric alcohol from the aqueous phase. Sulfided catalysts may be particularly advantageous in this regard, since they may experience minimal loss in their catalytic activity when present in an aqueous phase that is being distilled. Regardless of how separation takes place, the slurry catalyst may subsequently be returned to the cellulosic biomass solids, if desired. If needed, the slurry catalyst may be regenerated before or while being returned to the cellulosic biomass solids.

In various embodiments, the condensation reaction may take place at a temperature ranging between about 5° C. and about 500° C. The condensation reaction may take place in a condensed phase (e.g., a liquor phase) or in a vapor phase. For condensation reactions taking place in a vapor phase, the temperature may range between about 75° C. and about 500° C., or between about 125° C. and about 450° C. For condensation reactions taking place in a condensed phase, the temperature may range between about 5° C. and about 475° C., or between about 15° C. and about 300° C., or between about 20° C. and about 250° C.

In various embodiments, the higher molecular weight compound produced by the condensation reaction may comprise $\geq C_4$ hydrocarbons. In some or other embodiments, the higher molecular weight compound produced by the condensation reaction may comprise $\geq C_6$ hydrocarbons In some embodiments, the higher molecular weight compound produced by the condensation reaction may comprise $C_4$-$C_{30}$ hydrocarbons. In some embodiments, the higher molecular weight compound produced by the condensation reaction may comprise $C_6$-$C_{30}$ hydrocarbons. In still other embodiments, the higher molecular weight compound produced by the condensation reaction may comprise $C_4$-$C_{24}$ hydrocarbons, or $C_6$-$C_{24}$ hydrocarbons, or $C_4$-$C_{18}$ hydrocarbons, or $C_6$-$C_{18}$ hydrocarbons, or $C_4$-$C_{12}$ hydrocarbons, or $C_6$-$C_{12}$ hydrocarbons. As used herein, the term "hydrocarbons" refers to compounds containing both carbon and hydrogen without reference to other elements that may be present. Thus, heteroatom-substituted compounds are also described herein by the term "hydrocarbons."

The particular composition of the higher molecular weight compound produced by the condensation reaction may vary depending on the catalyst(s) and temperatures used for both the catalytic reduction reaction and the condensation reaction, as well as other parameters such as pressure. For example, in some embodiments, the product of the condensation reaction may comprise $\geq C_4$ alcohols and/or ketones that are produced concurrently with or in lieu of $\geq C_4$ hydrocarbons. In some embodiments, the $\geq C_4$ hydrocarbons produced by the condensation reaction may contain various olefins in addition to alkanes of various sizes, typically branched alkanes. In still other embodiments, the ≥$C_4$ hydrocarbons produced by the condensation reaction may also comprise cyclic hydrocarbons and/or aromatic compounds. In some embodiments, the higher molecular weight compound produced by the condensation reaction may be further subjected to a catalytic reduction reaction to transform a carbonyl functionality therein to an alcohol and/or a hydrocarbon and to convert olefins into alkanes.

Exemplary compounds that may be produced by a condensation reaction include, for example, ≥$C_4$ alkanes, ≥$C_4$ alkenes, ≥$C_5$ cycloalkanes, ≥$C_5$ cycloalkenes, aryls, fused aryls, ≥$C_4$ alcohols, ≥$C_4$ ketones, and mixtures thereof. The ≥$C_4$ alkanes and ≥$C_4$ alkenes may range from 4 to about 30 carbon atoms (i.e. $C_4$-$C_{30}$ alkanes and $C_4$-$C_{30}$ alkenes) and may be branched or straight chain alkanes or alkenes. The ≥$C_4$ alkanes and ≥$C_4$ alkenes may also include fractions of $C_7$-$C_{14}$, $C_{12}$-$C_{24}$ alkanes and alkenes, respectively, with the $C_7$-$C_{14}$ fraction directed to jet fuel blends, and the $C_{12}$-$C_{24}$ fraction directed to diesel fuel blends and other industrial applications. Examples of various ≥$C_4$ alkanes and ≥$C_4$ alkenes that may be produced by the condensation reaction include, without limitation, butane, butene, pentane, pentene, 2-methylbutane, hexane, hexene, 2-methylpentane, 3-methylpentane, 2,2-dimethylbutane, 2,3-dimethylbutane, heptane, heptene, octane, octene, 2,2,4,-trimethylpentane, 2,3-dimethylhexane, 2,3,4-trimethylpentane, 2,3-dimethylpentane, nonane, nonene, decane, decene, undecane, undecene, dodecane, dodecene, tridecane, tridecene, tetradecane, tetradecene, pentadecane, pentadecene, hexadecane, hexadecene, heptyldecane, heptyldecene, octyldecane, octyldecene, nonyldecane, nonyldecene, eicosane, eicosene, uneicosane, uneicosene, doeicosane, doeicosene, trieicosane, trieicosene, tetraeicosane, tetraeicosene, and isomers thereof.

The ≥$C_5$ cycloalkanes and ≥$C_5$ cycloalkenes may have from 5 to about 30 carbon atoms and may be unsubstituted, mono-substituted or multi-substituted. In the case of mono-substituted and multi-substituted compounds, the substituted group may include a branched ≥$C_3$ alkyl, a straight chain ≥$C_1$ alkyl, a branched ≥$C_3$ alkylene, a straight chain ≥$C_1$ alkylene, a straight chain ≥$C_2$ alkylene, an aryl group, or a combination thereof. In some embodiments, at least one of the substituted groups may include a branched $C_3$-$C_{12}$ alkyl, a straight chain $C_1$-$C_{12}$ alkyl, a branched $C_3$-$C_{12}$ alkylene, a straight chain $C_1$-$C_{12}$ alkylene, a straight chain $C_2$-$C_{12}$ alkylene, an aryl group, or a combination thereof. In yet other embodiments, at least one of the substituted groups may include a branched $C_3$-$C_4$ alkyl, a straight chain $C_1$-$C_4$ alkyl, a branched $C_3$-$C_4$ alkylene, a straight chain $C_1$-$C_4$ alkylene, a straight chain $C_2$-$C_4$ alkylene, an aryl group, or any combination thereof. Examples of ≥$C_5$ cycloalkanes and ≥$C_5$ cycloalkenes that may be produced by the condensation reaction include, without limitation, cyclopentane, cyclopentene, cyclohexane, cyclohexene, methylcyclopentane, methylcyclopentene, ethylcyclopentane, ethylcyclopentene, ethylcyclohexane, ethylcyclohexene, and isomers thereof.

The moderate fractions of the condensation reaction, such as $C_7$-$C_{14}$, may be separated for jet fuel, while heavier fractions, such as $C_{12}$-$C_{24}$, may be separated for diesel use. The heaviest fractions may be used as lubricants or cracked to produce additional gasoline and/or diesel fractions. The ≥$C_4$ compounds may also find use as industrial chemicals, whether as an intermediate or an end product. For example, the aryl compounds toluene, xylene, ethylbenzene, para-xylene, meta-xylene, and ortho-xylene may find use as chemical intermediates for the production of plastics and other products. Meanwhile, $C_9$ aromatic compounds and fused aryl compounds, such as naphthalene, anthracene, tetrahydronaphthalene, and decahydronaphthalene, may find use as solvents or additives in industrial processes.

In some embodiments, a single catalyst may mediate the transformation of the monohydric alcohol into a form suitable for undergoing a condensation reaction as well as mediating the condensation reaction itself. In other embodiments, a first catalyst may be used to mediate the transformation of the monohydric alcohol into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows.

In some embodiments, a single catalyst may be used to form a higher molecular weight compound via a condensation reaction. Without being bound by any theory or mechanism, it is believed that such catalysts may mediate an initial dehydrogenation of the alcoholic component, followed by a condensation reaction of the dehydrogenated alcoholic component. Zeolite catalysts are one type of catalyst suitable for directly converting alcohols to condensation products in such a manner. A particularly suitable zeolite catalyst in this regard may be ZSM-5, although other zeolite catalysts may also be suitable.

In some embodiments, two catalysts may be used to form a higher molecular weight compound via a condensation reaction. Without being bound by any theory or mechanism, it is believed that the first catalyst may mediate an initial dehydrogenation of the alcoholic component, and the second catalyst may mediate a condensation reaction of the dehydrogenated alcoholic component. Like the single-catalyst embodiments discussed previously above, in some embodiments, zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired.

In some embodiments, the condensation catalyst may comprise a basic catalyst comprising Li, Na, K, Cs, B, Rb, Mg, Ca, Sr, Si, Ba, Al, Zn, Ce, La, Y, Sc, Y, Zr, Ti, hydrotalcite, zinc-aluminate, phosphate, base-treated aluminosilicate zeolite, a basic resin, basic nitride, alloys or any combination thereof. In some embodiments, the basic catalyst may also comprise an oxide of Ti, Zr, V, Nb, Ta, Mo, Cr, W, Mn, Re, Al, Ga, In, Co, Ni, Si, Cu, Zn, Sn, Cd, Mg, P, Fe, or any combination thereof. In some embodiments, the basic catalyst may comprise a mixed-oxide basic catalyst. Suitable mixed-oxide basic catalysts may comprise, for example, Si—Mg—O, Mg—Ti—O, Y—Mg—O, Y—Zr—O, Ti—Zr—O, Ce—Zr—O, Ce—Mg—O, Ca—Zr—O, La—Zr—O, B—Zr—O, La—Ti—O, B—Ti—O, and any combination thereof. In some embodiments, the condensation catalyst may further include a metal or alloys comprising metals such as, for example, Cu, Ag, Au, Pt, Ni, Fe, Co, Ru, Zn, Cd, Ga, In, Rh, Pd, Ir, Re, Mn, Cr, Mo, W, Sn, Bi, Pb, Os, alloys and combinations thereof. Use of metals in the condensation catalyst may be desirable when a dehydrogenation reaction is to be carried out in concert with the condensation reaction. Basic resins may include resins that exhibit basic functionality. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a hydrotalcite material derived from a combination of MgO and $Al_2O_3$. In some embodiments, the condensation catalyst may comprise a zinc aluminate spinel formed from a combination of ZnO and $Al_2O_3$. In still other embodiments, the condensation catalyst may comprise a combination of ZnO, $Al_2O_3$, and CuO. Each of these materials may also contain an additional metal or alloy, including those more generally referenced above for basic condensation catalysts. In more particular embodiments, the additional metal or alloy may comprise a Group 10 metal such Pd, Pt, or any combination thereof.

In some embodiments, the condensation catalyst may comprise a basic catalyst comprising a metal oxide containing, for example, Cu, Ni, Zn, V, Zr, or any mixture thereof. In some or other embodiments, the condensation catalyst may comprise a zinc aluminate containing, for example, Pt, Pd, Cu, Ni, or any mixture thereof.

In some embodiments, the condensation catalyst may comprise a multi-functional catalyst having both an acidic functionality and a basic functionality. Such condensation catalysts may comprise a hydrotalcite, a zinc-aluminate, a phosphate, Li, Na, K, Cs, B, Rb, Mg, Si, Ca, Sr, Ba, Al, Ce, La, Sc, Y, Zr, Ti, Zn, Cr, or any combination thereof. In further embodiments, the multi-functional catalyst may also include one or more oxides from the group of Ti, Zr, V, Nb, Ta, Mo, Cr, W, Mn, Re, Al, Ga, In, Fe, Co, Ir, Ni, Si, Cu, Zn, Sn, Cd, P, and any combination thereof. In some embodiments, the multi-functional catalyst may include a metal such as, for example, Cu, Ag, Au, Pt, Ni, Fe, Co, Ru, Zn, Cd, Ga, In, Rh, Pd, Ir, Re, Mn, Cr, Mo, W, Sn, Os, alloys or combinations thereof. The basic catalyst may be self-supporting or adhered to a support containing a material such as, for example, carbon, silica, alumina, zirconia, titania, vanadia, ceria, nitride, boron nitride, a heteropolyacid, alloys and mixtures thereof.

In some embodiments, the condensation catalyst may comprise a metal oxide containing Pd, Pt, Cu or Ni. In still other embodiments, the condensation catalyst may comprise an aluminate or a zirconium metal oxide containing Mg and Cu, Pt, Pd or Ni. In still other embodiments, a multi-functional catalyst may comprise a hydroxyapatite (HAP) combined with one or more of the above metals.

In some embodiments, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and $ZrO_2$, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

In some embodiments, an acid catalyst may be used to optionally dehydrate at least a portion of the reaction product. Suitable acid catalysts for use in the dehydration reaction may include, but are not limited to, mineral acids (e.g., HCl, $H_2SO_4$), solid acids (e.g., zeolites, ion-exchange resins) and acid salts (e.g., $LaCl_3$). Additional acid catalysts may include, without limitation, zeolites, carbides, nitrides, zirconia, alumina, silica, aluminosilicates, phosphates, titanium oxides, zinc oxides, vanadium oxides, lanthanum oxides, yttrium oxides, scandium oxides, magnesium oxides, cerium oxides, barium oxides, calcium oxides, hydroxides, heteropolyacids, inorganic acids, acid modified resins, base modified resins, and any combination thereof. In some embodiments, the dehydration catalyst may also include a modifier. Suitable modifiers may include, for example, La, Y, Sc, P, B, Bi, Li, Na, K, Rb, Cs, Mg, Ca, Sr, Ba, and any combination thereof. The modifiers may be useful, inter alia, to carry out a concerted hydrogenation/dehydrogenation reaction with the dehydration reaction. In some embodiments, the dehydration catalyst may also include a metal. Suitable metals may include, for example, Cu, Ag, Au, Pt, Ni, Fe, Co, Ru, Zn, Cd, Ga, In, Rh, Pd, Ir, Re, Mn, Cr, Mo, W, Sn, Os, alloys, and any combination thereof. The dehydration catalyst may be self supporting, supported on an inert support or resin, or it may be dissolved in a fluid.

The methods described herein will now be described with further reference to the drawing. FIG. 1 shows a schematic of an illustrative biomass conversion system 1 in which a phenolics liquid phase may form and be further processed. As depicted in FIG. 1, cellulosic biomass solids may be introduced to hydrothermal digestion unit 2 via solids introduction mechanism 4. Solids introduction mechanism 4 may comprise loading mechanism 6 and pressure transition zone 8, which may elevate the cellulosic biomass solids from atmospheric pressure to a pressure near that of the operating pressure of hydrothermal digestion unit 2, thereby allowing continuous or semi-continuous introduction of cellulosic biomass solids to take place without fully depressurizing hydrothermal digestion unit 2. Suitable loading mechanisms and pressure transition zones have been described in more detail hereinabove.

Hydrothermal digestion unit 2 contains cellulosic biomass solids, a digestion solvent, and particulates of the slurry catalyst 10. In the interest of clarity, the cellulosic biomass solids have not been depicted in FIG. 1, but it is to be understood that at least a portion of the slurry catalyst particulates 10 are distributed within the cellulosic biomass solids. Upon digestion of the cellulosic biomass solids in the presence of the digestion solvent, phase separation occurs. Typically, a phenolics liquid phase occurs in zone 3 of hydrothermal digestion unit 2, and an aqueous phase containing an alcoholic component derived from the cellulosic biomass solids occurs in zone 5 of hydrothermal digestion unit 2. Depending on process conditions, a light organics phase may also occur in zone 7 of hydrothermal digestion unit 2.

Before digestion of the cellulosic biomass solids begins, the slurry catalyst particulates 10 may be distributed in the cellulosic biomass solids using fluid flow. After phase formation takes place, individual particulates of the slurry catalyst may be located at different points within hydrothermal digestion unit 2. Particularly, the slurry catalyst particulates 10 may accumulate in the phenolics liquid phase over time. Some of these slurry catalyst particulates 10 may be fluidized by upwardly directed fluid flow supplied by gas inlet line 9 or fluid return line 11.

The aqueous phase containing a glycol produced by an in situ catalytic reduction reaction process of soluble carbohydrates may be circulated through the cellulosic biomass solids. Specifically, the aqueous phase may exit hydrothermal digestion unit 2 via line 12 and travel via line 14 to fluid return line 11. The upwardly directed fluid flow provided by fluid return line 11 may promote fluidization of slurry catalyst particulates 10 in hydrothermal digestion unit 2. In some embodiments, slurry catalyst particulates 10 may travel with the aqueous phase as they flow through lines 11, 12, and 14.

Aqueous phase not being recirculated through lines 11, 12, and 14 may travel to separations unit 16 in which at least a portion of the water may be removed from the aqueous phase, thereby producing a dried glycol. Dried glycol produced in separations unit 16 may exit via line 17 and travel to lignin processing unit 24.

The phenolics liquid phase in hydrothermal digestion unit 2 may be removed therefrom via line 15 and travel to lignin processing unit 24. In lignin processing unit 24, the phenolics liquid phase may be mixed with the dried glycols produced in separations unit 16 to form a combined phase. Transfer of the phenolics liquid phase to lignin processing unit 24 may occur continuously or on an as-needed basis. Thermal treatment of the combined phase may thereafter take place continuously or on an as-needed basis to reduce the viscosity of the combined phase in lignin processing unit 24. Particularly, reduction of the viscosity may at least partially depolymerize the lignin present therein. As described above, the thermal treatment may also convert at least a portion of the glycol in the combined phase into a monohydric alcohol. Furthermore, in some embodiments, methanol may be produced in lignin processing unit 24 in conjunction with converting the glycol into a monohydric alcohol.

Dried monohydric alcohol and/or methanol produced in lignin processing unit 24 may thereafter exit therefrom. In some embodiments, a portion of the monohydric alcohol may be returned to hydrothermal digestion unit 2 via lines 23 and 11. Return of a dried monohydric alcohol to hydrothermal digestion unit 2 may desirably modify the composition of the digestion solvent. In addition to the dried monohydric alcohol, slurry catalyst and/or the deviscosified phenolics liquid phase may be returned to hydrothermal digestion unit 2 via lines 23 and 11. In some or other embodiments, the slurry catalyst may be regenerated, if needed, prior to being returned to hydrothermal digestion unit 2.

Dried monohydric alcohol and/or methanol not being returned to hydrothermal digestion unit 2 may be removed from lignin processing unit 24 via line 26 and conveyed to reforming reactor 28. Optionally, reaction products arising from lignin depolymerization (e.g., phenolic compounds) may also be conveyed to reforming reactor 28 along with the monohydric alcohol and/or methanol for further processing.

In reforming reactor 28, a condensation reaction or other reforming reaction may take place. The reforming reaction taking place therein may be catalytic or non-catalytic. Although only one reforming reactor 28 has been depicted in FIG. 1, it is to be understood that any number of reforming reactors may be present. In reforming reactor 28, one or more further reforming reactions may take place, as described above. In some embodiments, a first reforming reaction may comprise a condensation reaction. Additional reforming reactions may comprise any combination of further catalytic reduction reactions (e.g., hydrogenation reactions, hydrogenolysis reactions, hydrotreating reactions, and the like), further condensation reactions, isomerization reactions, desulfurization reactions, dehydration reactions, oligomerization reactions, alkylation reactions, and the like. Such transformations may be used to convert the initially produced soluble carbohydrates into a biofuel. Such biofuels may include, for example, gasoline hydrocarbons, diesel fuels, jet fuels, and the like. As used herein, the term "gasoline hydrocarbons" refers to substances comprising predominantly $C_5$-$C_9$ hydrocarbons and having a boiling point of 32° C. to about 204° C. More generally, any fuel blend meeting the requirements of ASTM D2887 may be classified as a gasoline hydrocarbon. Suitable gasoline hydrocarbons may include, for example, straight run gasoline, naphtha, fluidized or thermally catalytically cracked gasoline, VB gasoline, and coker gasoline. As used herein, the term "diesel fuel" refers to substances comprising paraffinic hydrocarbons and having a boiling point ranging between about 187° C. and about 417° C., which is suitable for use in a compression ignition engine. More generally, any fuel blend meeting the requirements of ASTM D975 may also be defined as a diesel fuel. As used herein, the term "jet fuel" refers to substances meeting the requirements of ASTM D1655. In some embodiments, jet fuels may comprise a kerosene-type fuel having substantially $C_8$-$C_{16}$ hydrocarbons (Jet A and Jet A-1 fuels). In other embodiments, jet fuels may comprise a wide-cut or naphtha-type fuel having substantially $C_5$-$C_{15}$ hydrocarbons present therein (Jet B fuels).

To facilitate a better understanding of the present invention, the following examples of preferred embodiments are given. In no way should the following examples be read to limit, or to define, the scope of the invention.

EXAMPLES

Example 1

Formation and Thermal Treatment of a Phenolics Liquid Phase in the Presence of an Aqueous Phase A 100 mL Parr reactor was charged with a solvent mixture comprising 29.3 grams of 1,2-propylene glycol, 3.3 grams of ethylene glycol, and 32.5 grams of deionized water. 0.752 grams of nickel-oxide promoted cobalt molybdate catalyst was then added (DC-2534, Criterion Catalyst & Technologies L.P., containing 1-10% cobalt oxide and molybdenum trioxide (up to 30 wt. %) on alumina, and less than 2% nickel). The catalyst was previously sulfided as described in United States Patent Application Publication 2010/0236988, which is incorporated herein by reference in its entirety. The reactor was then charged with 6.05 grams of southern pine mini-chips (39% moisture, nominal dimensions of 3 mm×5 mm×5 mm) and 0.18 grams of potassium carbonate buffer, before pressurizing with 765 psia of hydrogen. The stirred reactor was heated to 190° C. for 1 hour, followed by ramping over 15 minutes to a temperature of 250° C. and holding to complete a 5 hour cycle. At the end of the cycle, a liquid sample was withdrawn via a 0.5 micron dip tube. The mass of the liquid sample corresponded approximately to the mass of the wood feed initially added, thereby maintaining a constant reactor inventory. The reactor was cooled, depressurized, and another charge of wood chips was added to initiate the next reaction cycle.

The above sequence was repeated for 17 cycles, with the addition of 100.7 grams of wood chips in total. At this cycle, the 0.5 micron filter plugged, such that only 2.32 grams of liquid sample were obtained over 10 minutes at a pressure differential of 1264 psia. Reactor samples comprised a viscous, phenolic-rich lower layer (verified by gas chromatographic mass spec (GCMS) analysis) and an aqueous layer comprising solvent and water-soluble oxygenated and alkane hydrocarbon products derived from the wood feed. For some samples, a small alkane-rich oil layer was also observed. The aqueous and oil layers were analyzed by gas chromatography using a 60 m×0.32 mm ID DB-5 column of 1 μm thickness, with 50:1 split ratio, 2 mL/min helium flow, and column oven held at 40° C. for 8 minutes, followed by ramp to 285° C. at 10° C./min, and a hold time of 53.5 minutes. The injector temperature was set at 250° C., and the detector temperature was set at 300° C. A range of alkanes, mono-oxygenated aldehyde and ketones, glycols, and polyols were observed in the aqueous phase, each with a volatility greater than the $C_6$ sugar alcohol sorbitol. Ethylene glycol, 1,2-propylene glycol, and glycerol were all observed.

The reactor was then heated to 270° C. for 4 hours, after which a 5.12 gram sample was obtained in less than 5 seconds at a pressure differential of 1241 psi. GC analysis indicated the formation of ethanol, 1-propanol, and 2-propanol via the elevated temperature treatment, demonstrating conversion of propylene glycol and ethylene glycol to mono-oxygenated compounds. Falling film viscosity tests of the phenolics liquid phase before and after heating to 270° C. indicated a reduction in viscosity from an estimated initial viscosity of greater than 10,000 cP at 110° C. (no flow), to a viscosity of approximately 1000 cP after treatment. Thus, within the same operation, thermal treatment of the reactor contents unplugged the sintered metal filter, reduced the viscosity, and formed mono-oxygenated compounds.

Example 2

Viscosity of the Phenolics Liquid Phase

The cycles for Example 1 were repeated through cycle 29, after which a one gram sample of the phenolics liquid phase was placed in a 1 ounce vial and allowed to cool to room temperature. No flow was observed upon tipping of the vial by 90 degrees. The vial was heated to 110° C. in a block heater, but again no flow was observed. The viscosity at 110° C. was too large to measure and estimated to be greater than 10,000 cP, based on flow behavior observed in an analogous test with high viscosity model fluid. Acetone solubility of the phenolics liquid phase at a 10:1 solvent/sample ratio was negligible.

After charging with 750 psig of hydrogen, the reactor was heated at 270° C. for 23.5 hours after a normal 5 hour cycle. After hydrotreating, a sample of the phenolics liquid phase exhibited a falling film viscosity comparable to that of glycerol (approximately 1000 cP at 25° C.), after re-heating to 108° C. in a block heater. Upon tipping a vial containing the hydrotreated phenolics liquid phase by 90 degrees, the phenolics liquid phase readily flowed to form a flat layer on the side of the vial within 3 seconds. 0.1 grams of the hydrotreated phase were dissolved in acetone and analyzed by GCMS. While much of the dissolved phase remained too heavy to elute from the GC column, formation of 2-methoxy-4-propylphenol was observed.

Example 3

Multi-Cycle Reaction with No Thermal Treatment

A 100 mL Parr reactor was charged with 60.18 grams of deionized water solvent and 0.754 grams of the sulfided nickel-oxide promoted cobalt molybdate catalyst described in Example 1. The reactor was charged with 5.05 grams of southern pine mini-chips (39% moisture having nominal dimensions of 3 mm×5 mm×5 mm) and 0.195 grams of potassium carbonate buffer, before pressurizing with 766 psia of hydrogen. The stirred reactor was heated to 190° C. for 1 hour before ramping over 15 minutes to a temperature of 250° C. and holding to complete a 5 hour cycle. Reaction products including mono-oxygenated compounds, glycerol, propylene glycol, ethylene glycol, and other oxygenated, alkane and organic acids were observed. Subsequent cycles were conducted as described in Example 1.

After eight cycles, the 0.5 micron sintered metal dip tube plugged, and it was not possible to sample the mixed reaction phases. After cool down, a bottoms phase was removed that could not be made to flow upon reheating to 110° C., indicating a viscosity of greater than 10,000 cP.

Example 4

Multi-Cycle Reaction with Thermal Treatment in the Presence of an Aqueous Phase

Example 3 was repeated with 1.8 grams of catalyst and a temperature ramp to 270° C. for 1.5 hours at the end of a normal 5 hour total cycle. GC analysis indicated the formation of methanol, other mono-oxygenated compounds, and some residual glycols and higher oxygenated compounds. Glycols and higher oxygenated compound concentrations were less than for Example 3, indicating an increased conversion to mono-oxygenated compounds. No filter plugging was observed for 10 cycles, and samples of the phenolics liquid phase showed a falling film viscosity of less than 1000 cP at 110° C. GCMS analysis indicated the presence of a propyl phenol.

Example 5

Thermal Treatment of a Phenolics Liquid Phase in the Absence of an Aqueous Phase A Parr5000 reactor was charged with 20 grams of 45% 1,2-propylene glycol/5% ethylene glycol in deionized water solvent. 0.30 grams of the sulfided cobalt molybdate catalyst from Example 1 and 0.12 grams of potassium carbonate buffer were added. 2.7 grams of southern pine mini-chips (39% moisture having nominal dimensions of 3 mm×5 mm×5 mm) were then added. The reactor was pressurized with 51 bar of hydrogen and heated to 190° C. for 1 hour, followed by heating to 250° C. to complete a 5 hour reaction cycle. At the end of each cycle, the reactor was allowed to cool and phase separate overnight before opening to sample. A sample of the aqueous layer was removed via pipet after each cycle, and an approximately equivalent amount of wood chips was added for the next cycle to maintain the liquid level in the reactor. The aqueous samples after overnight settling were clear and free of catalyst.

The above reaction sequence was continued through 16 cycles, and the remaining aqueous phase was then removed by pipet. An estimated 10 grams of phenolics liquid phase remained, which did not flow upon heating to 110° C., leading to an estimated viscosity of higher than 10,000 cP. 20.43 grams of 90% 1,2-propylene glycol/10% ethylene glycol were added to the reactor. The reactor was then pressurized to 50 bar with hydrogen and heated to 270° C. for 18 hours. The resulting mixture formed a single phase with a viscosity of less than 1000 cP. GC analysis indicated conversion of 1,2- propylene glycol and ethylene glycol was more than 54%, with formation of 1-propanol, ethanol, acetone, and other oxygenated products being observed. By conducting the thermal treatment in the absence of an aqueous phase, a single-phase mixture was observed.

Excess solvent was removed after settling of the catalyst, and an additional 10 cycles of wood chip addition were conducted as described above. The catalyst remained active for forming oxygenated compounds from the wood chips.

Example 6

Use of Glycerol as a Digestion Solvent

A 75 mL Parr5000 reactor was charged with 15.08 grams of glycerol, 15.05 grams of deionized water, 0.124 grams of potassium carbonate buffer, and 0.302 grams of the cobalt molybdate catalyst from Example 1. The initial glycerol concentration was 50 wt. %. The reactor was pressurized to 53 bar with hydrogen and heated to 220° C. for 18 hours, during which time 44% of the glycerol was converted to glycols and other oxygenated products, with ethylene glycol and 1,2-propylene glycol comprising about 35% by weight of the products formed.

The reaction product mixture with catalyst was distilled at atmospheric pressure under a blanket of nitrogen, at a bottoms temperature of 130-156° C. and a tops distillate temperature of 92-98.4° C., in a short-path still. GC analysis of the tops distillate products revealed 47.8% by weight of the original water was removed via flash distillation. The distillate composition was 91% water, with a small concentration of mono-oxygenated products. An initial cut of light solvent from the above distillation analyzed as 61% water and 39% light mono-oxygenated compounds (ethanol, 1-propanol, 2-propanol, and acetone), thereby illustrating the difficulty in recycling a dry mono-oxygenated solvent via flash distillation from water. The water concentration in the distillation bottoms was 35.4%.

The bottoms product from distillation, with catalyst, was recycled back to the Parr5000 reactor, and subjected to a second reaction cycle with addition of 2.7 grams of soft pine wood chips (39% moisture). The reactor was heated to 190° C. for 1 hour, followed by heating to 230° C. for 4 hours. Conversion of glycerol was 25%, and digestion and conversion of the wood was complete. The reaction rate for glycerol conversion with the recycled catalyst was comparable to that seen before distillation was conducted.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods may also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   providing cellulosic biomass solids in the presence of a digestion solvent, molecular hydrogen, and a slurry catalyst capable of activating molecular hydrogen;
   at least partially converting the cellulosic biomass solids into a phenolics liquid phase comprising lignin, an aqueous phase comprising a glycol derived from the cellulosic biomass solids, and an optional light organics phase;
   wherein at least a portion of the slurry catalyst accumulates in the phenolics liquid phase as it forms;
   combining the glycol with the phenolics liquid phase, thereby forming a combined phase; and
   heating the combined phase in the presence of molecular hydrogen;
   wherein heating the combined phase reduces the viscosity of the phenolics liquid phase and transforms at least a portion of the glycol into a monohydric alcohol.

2. The method of claim 1, wherein the glycol is formed by a catalytic reduction reaction of soluble carbohydrates, the soluble carbohydrates being derived from the cellulosic biomass solids.

3. The method of claim 1, wherein the slurry catalyst comprises a poison-tolerant catalyst.

4. The method of claim 3, wherein the poison-tolerant catalyst comprises a sulfided catalyst.

5. The method of claim 1, wherein heating the combined phase in the presence of molecular hydrogen at least partially depolymerizes the lignin therein.

6. The method of claim 5, wherein the cellulosic biomass solids are heated to a first temperature to form the phenolics liquid phase and the aqueous phase, and the combined phase is heated to a second temperature to at least partially depolymerize the lignin, the first temperature being lower than the second temperature and insufficient to at least partially depolymerize the lignin.

7. The method of claim 1, further comprising:
   separating the phenolics liquid phase from the cellulosic biomass solids before combining the glycol with the phenolics liquid phase.

8. The method of claim 7, further comprising:
   removing at least a portion of the water from the aqueous phase, thereby producing a dried glycol;
   wherein the dried glycol is combined with the phenolics liquid phase.

9. The method of claim 8, wherein removing at least a portion of the water from the aqueous phase comprises a distillation to separate at least a portion of the water from the glycol.

10. The method of claim 1, further comprising:
separating the phenolics liquid phase from the aqueous phase; and
after separating the phenolics liquid phase from the aqueous phase, removing at least a portion of the water from the aqueous phase, thereby producing a dried glycol;
wherein the dried glycol is combined with the phenolics liquid phase.

11. The method of claim 10, wherein removing at least a portion of the water from the aqueous phase comprises a distillation to separate at least a portion of the water from the glycol.

12. The method of claim 1, wherein the combined phase is heated to a temperature of about 270° C. or higher.

13. The method of claim 1, further comprising:
measuring the viscosity of the phenolics liquid phase; and
heating the combined phase until a desired viscosity has been reached.

14. The method of claim 1, further comprising:
forming methanol from the lignin while heating the combined phase.

15. The method of claim 14, further comprising:
separating the methanol and the monohydric alcohol from the combined phase.

16. The method of claim 15, further comprising:
performing a condensation reaction on the methanol and the monohydric alcohol or a product derived therefrom.

17. The method of claim 1, further comprising:
separating the monohydric alcohol from the combined phase.

18. The method of claim 17, further comprising:
performing a condensation reaction on the monohydric alcohol or a product derived therefrom.

19. The method of claim 1, further comprising:
separating the slurry catalyst from the combined phase after reducing the viscosity.

20. The method of claim 19, further comprising:
returning the slurry catalyst to the cellulosic biomass solids.

21. The method of claim 1, further comprising:
circulating at least a portion of the aqueous phase through the cellulosic biomass solids.

22. A method comprising:
providing cellulosic biomass solids in the presence of a digestion solvent, molecular hydrogen, and a slurry catalyst capable of activating molecular hydrogen;
heating the cellulosic biomass solids to a first temperature and forming a phenolics liquid phase comprising lignin, an aqueous phase comprising a glycol derived from the cellulosic biomass solids, and an optional light organics phase;
wherein at least a portion of the slurry catalyst accumulates in the phenolics liquid phase as it forms;
separating the phenolics liquid phase from the aqueous phase and the cellulosic biomass solids;
removing at least a portion of the water from the aqueous phase, thereby producing a dried glycol;
combining the dried glycol with the phenolics liquid phase, thereby forming a combined phase; and
heating the combined phase to a second temperature in the presence of molecular hydrogen, the second temperature being sufficient to reduce the viscosity of the phenolics liquid phase and transform at least a portion of the dried glycol into a monohydric alcohol;
wherein the first temperature is lower than the second temperature.

23. The method of claim 22, wherein the glycol is formed by a catalytic reduction reaction of soluble carbohydrates, the soluble carbohydrates being derived from the cellulosic biomass solids.

24. The method of claim 22, wherein the slurry catalyst comprises a poison-tolerant catalyst.

25. The method of claim 24, wherein the poison-tolerant catalyst comprises a sulfided catalyst.

26. The method of claim 22, wherein heating the combined phase to the second temperature in the presence of molecular hydrogen at least partially depolymerizes the lignin therein.

27. The method of claim 26, wherein the first temperature is insufficient to at least partially depolymerize the lignin.

28. The method of claim 26, wherein the second temperature is about 270° C. or higher.

29. The method of claim 28, wherein the first temperature is about 250° C. or lower.

30. The method of claim 22, further comprising:
measuring the viscosity of the phenolics liquid phase; and
heating the combined phase until a desired viscosity has been reached.

31. The method of claim 22, further comprising:
forming methanol from the lignin while heating the combined phase.

32. The method of claim 31, further comprising:
separating the methanol and the monohydric alcohol from the combined phase.

33. The method of claim 32, further comprising:
performing a condensation reaction on the methanol and the monohydric alcohol or a product derived therefrom.

34. The method of claim 22, further comprising:
separating the monohydric alcohol from the combined phase.

35. The method of claim 34, further comprising:
performing a condensation reaction on the monohydric alcohol or a product derived therefrom.

36. The method of claim 22, further comprising:
separating the slurry catalyst from the combined phase after heating to the second temperature.

37. The method of claim 36, further comprising:
returning the slurry catalyst to the cellulosic biomass solids.

38. The method of claim 22, further comprising:
circulating at least a portion of the aqueous phase through the cellulosic biomass solids.

* * * * *